US010228380B2

(12) United States Patent
Yamanaka et al.

(10) Patent No.: US 10,228,380 B2
(45) Date of Patent: Mar. 12, 2019

(54) METHODS FOR TARGETING MEMBRANE STEROID TRANSPORTERS

(71) Applicant: The Regents of the University of California, Oakland, CA (US)

(72) Inventors: Naoki Yamanaka, Riverside, CA (US); Sachiko Yamanaka, Riverside, CA (US); Naoki Okamoto, Riverside, CA (US); Riyan Bittar, South Pasadena, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/902,948

(22) Filed: Feb. 22, 2018

(65) Prior Publication Data

US 2018/0372760 A1  Dec. 27, 2018

(51) Int. Cl.
*G01N 33/74* (2006.01)

(52) U.S. Cl.
CPC ....... *G01N 33/743* (2013.01); *G01N 2500/04* (2013.01)

(58) Field of Classification Search
USPC ........................................................ 435/6.13
See application file for complete search history.

(56) References Cited

U.S. PATENT DOCUMENTS 6,680,379 B1 * 1/2004 Sun ..................... C07K 14/705
                                                  435/320.1
2005/0159352 A1   7/2005 Friesema et al.
2009/0081212 A1   3/2009 Shi et al.

OTHER PUBLICATIONS

Yang et al., SLCO2B1 and SLCO1B3 May Determine Time to Progression for Patients Receiving Androgen Deprivation Therapy for Prostate Cancer, 2011, J Clin Oncol 29:2565-2573.*
Harshman et al., Statin Use at the Time of Initiation of Androgen Deprivation Therapy and Time to Progression in Patients With Hormone-Sensitive Prostate Cancer, 2015, JAMA Oncol. 2015;1(4):495-504.*
Hock et al., The E23 early gene of *Drosophila* encodes an ecdysone-inducible ATP-binding cassette transporter capable of repressing ecdysonemediated gene activation, PNAS, Aug. 15, 2000, vol. 97, No. 17, 9519-9524.*
Crouch et al., The use of ATP bioluminescence as a measure of cell proliferation and cytotoxicity, J Immunol Methods. Mar. 15, 1993;160(1):81-8.*
Bossuyt et al., "Polyspecific Drug and Steroid Clearance by An Organic Anion Transporter of Mammalian Liver", *The Journal of Pharmacology and Experimental Therapeutics*, vol. 276, No. 3, 1996, pp. 891-896.
Buxhofer-Ausch et al., "Tumor-Specific Expression of Organic Anion-Transporting Polypeptides: Transporters as Novel Targets for Cancer Therapy", Journal of Drug Delivery, vol. 2013, 2013, pp. 1-12.
Green et al., "Role of OATP Transporters in Steroid Uptake by Prostate Cancer Cells in Vivo". *Prostate Cancer Prostatic Dis.*, vol. 20, No. 1, Mar. 2017, pp. 20-27.

* cited by examiner

*Primary Examiner* — Antonio Galisteo Gonzalez
(74) *Attorney, Agent, or Firm* — Morrison and Foerster LLP

(57) ABSTRACT

Described herein are methods of identifying compounds that can modulate the transport of a steroid hormone across a phospholipid membrane. Also described herein are methods of identifying compounds that can affect the transcriptional activity of a steroid hormone nuclear receptor.

20 Claims, 7 Drawing Sheets

Specification includes a Sequence Listing.

SEQUENCE LISTING

```
<160> NUMBER OF SEQ ID NOS: 3

<210> SEQ ID NO 1
<211> LENGTH: 3699
<212> TYPE: DNA
<213> ORGANISM: Drosophila melanogaster

<400> SEQUENCE: 1
ttaccgtgtg cggactgtgc cgacgggcag cggaactcag gcggtgcaac ttgagtgctt      60
gataaatttg ttgtattgaa acccaaccgc aaatacaatt ttcaattggc tgagtgcgtg     120
tcttcaacgc acaaacatac gaatatagca tttaatattg ttcattatgt gtgcaattaa     180
ataaaaaaaa ttgtgtgtga aataacagaa aaacgagtgc ggcgaacaga ggcagcaaca     240
aattaaacgc gtaaattgcg tagcaaattc tgaatgaaaa aattcaacaa aaccagaaag     300
```

```
cgaaacagga gcgataagct taccaactaa agaaactcac gcctaacaga aatacacacc    360
actgccatat taaagcaaag aatatagaac tgttttacag accagatcaa ccaatctacc    420
tcgacttctg ggccaacaag caaaataaaa ctaaactcaa tgccagaacc caatttcccg    480
ataggaaaat ggaacaggca ataagcaaga ccacatagag gagattaact aaacggatcc    540
gttgagatta cacagttgag atcaataaaa cccattgaag atcgatcaaa ccatctagtt    600
ttttagagtt ccattagaag ccaaaatgac gaagagcaat ggcgatgtgg aggcggcagc    660
ccaggtgcaa tctctgggcg gaaagcccag caacggacat ggccagctga atgggaatgg    720
ctatcatcag aacggcggac gcagggattc cagtcaagcc ttcacaccac tgctgtcgca    780
gcacaataat ggcaccacca atggcgaggt gaccactccg cctccgagta cagtgctcta    840
cgagagcacc ccgagcaata taacgagtg gaaggcccg gaggatctgg acacctgaa    900 gaatggcctg ggcaacatac tgagcagtaa taataatggc accggcaatg ggcacagtct    960
gagcgaaaag tatgcccatg aacaggctcc cctgaccgga ggttacaagt tgccacctcg    1020
ctccagtgag tccgaggaat ccgatttcga ttccgacctc aatggcggct cctccgcgga    1080
atccagctcc agttgcggcc ttttcggctg tcggcccagg tgggccagaa gattcgcgtc    1140
cacgcacgtc ttcatggtgg tcttcctgct ggcctacatc ctgcagggca tgtacatgac    1200
ctacttcgtc tctgtgatca ccaccattga gaagctattc cagatcaagt cgaagaccac    1260
gggaattctg ctgagcgcca gtgagatggg tcagatatgc acggccatgt tgctgaccta    1320
cttcgccggc agaggacatc gtccgagatg gattgcctgc ggcatggtcc tgttctcaat    1380
cgccgccttc tcctgcgccc tgccgcattt catcttcggc gagcagctga tgcactccag    1440
tgtaattctg cagcagacgc aggtctcccc ccccaataat tccttctcat cacactggct    1500
gaatgccagc agtgaacagg ttaatcccaa tttgtgcatt ttgggtggca accaaaccca    1560
ttcgggcagc gagtgcaacg aggagcgcca gctggaacag gcctcccact ctaagatcac    1620
cgtcatcgtg ctgtgcatct tctttggcag cctgctcagc tcgggcattg ccagaccgc    1680 cgtggccaca ctgggcatac cctacatcga tgacaatgta ggcagcaagc agtcgcccat    1740
gtacatggcc gtcaccattg gcatgaggat cctgggaccg gcatccggtt tcatttttgg    1800
cagcttctgc actcgctggt atgtcaactt ctcgaatccc ggcttcgacg ccacggatcc    1860
gcgctggatt ggcgcctggt ggctggggcc tgtggccatt ggcagcctca tgctgctggc    1920
ctccatcgcc atgttctcgt tcccaagca gttgagaggc aagcagaagc cgccggggca    1980
gacagcaact ccagcagctc cagttgagcc ggaggagaag cccaagctaa agatttcc    2040 caagacagtc cgtcgccagc tgagcaacga catcctgatg ttccgcaccg cctcgtgcgt    2100
gttccacctg ctgcccatcg ccggtctcta tacgttcctg cccaagtatc tggagacgca    2160
gttccggctg gccacctatg atgccaacat gatcgccgcc ttctgtggca tcctggtcat    2220
gggcataggt attgtcattt ccgggctctt catcctgaag cgaaagccca ctgccagggg    2280
cgtggccgcc tggatcgcct ttacagccct cgtctactcg gcgggcatga tcatcctgat    2340
gttcatcggc tgcagcatga acgactttgc cggctacaag ccaagcgatg caacagtcc    2400 cgccttgatc gagcccacgt gcagtgccgc tctcaactgt acctgtgata aggagaactt    2460
cgcgcccatc tgcgccgacg gcaaaatgta catctcggcc tgccacgccg gatgcagcag    2520
ctcctcactg cggcccagcg acaatcgcac actctactcc gattgtgctt gcattccaga    2580
tgctccggag gcggtcaacg gttactgtga taataactga agaacttca tctactttat    2640 actgatcttt gccatttgcg tatttatgca ttccacctcc gaggtgggca gcatgctgct    2700
```

```
cgtcatgcgc tgcacacacc ccaaagataa ggccatggcc atgggtgtga tacagtcggc    2760
catcggcctg ttcggcaacg ttccctgtcc catcatctac ggcgcagtgg tggactccgc    2820
ctgcctcatc tggaagtcgg tgtgcggcaa gcacggcgcc tgttcactct acgatgcgga    2880
cactttccgg caatatttcc taggaatcac ggctggcatt atgttcctgg cattcctgat    2940
ggatctggtg gtgtggcgca aggcgcatcg cattgacatc gcgcccgagg atccgcagga    3000
gggcgggccc gcttccaacg gaaggacctt ggaggtgtcc gagtccaagc agcccatcac    3060
cccggcgccg gacacgacgg tctaggagga gcgggtcggc gacgagcctt gcacaagctg    3120
caggatttcc aataaacgtt taccttaatt gttaattagt tatcatttgt ctagtttgtt    3180
agcctagtgc aagagttatg tatttagtta agtggcatct tcgagcgtcg ggagacctca    3240
ttcaaatcca cattagaacg cgctcgtcca gctcccgctc ccgatcctgc tccaaatccc    3300
agcaccatat tctacatgaa gcccatggat tgcgatttga atccttgtaa atctcaacgc    3360
gaaacaatga aatgaaattc tagacattat ctaacgtcat gcatgagcgt agttaatcga    3420
cgagctaata ctacaaactg atcgacaatt gtgcaaagtg caagaaaatt tatgaatcct    3480
tatgtgtaaa ctatatgtaa cagttatatc gcgatgtatg taatctataa ttaatatatt    3540
agacatacac ttacatgtat gtatgtaatt gcaacctatc tgtggtagtt aaattttagt    3600
taaaattcaa attaattgtc taagtttgtc atacaacaaa tatatacgaa agaaattaa    3660 atggaaaact atatacaagt aaaaaaaaaa aaaaaaaa                           3699

<210> SEQ ID NO 2
<211> LENGTH: 2460
<212> TYPE: DNA
<213> ORGANISM: Drosophila melanogaster

<400> SEQUENCE: 2
atgacgaaga gcaatggcga tgtggaggcg gcagcccagg tgcaatctct gggcggaaag      60
cccagcaacg gacatggcca gctgaatggg aatggctatc atcagaacgg cggacgcagg     120
gattccagtc aagccttcac accactgctg tcgcagcaca ataatggcac caccaatggc     180
gaggtgacca ctccgcctcc gagtacagtg ctctacgaga gcaccccgag caataataac     240
gagtggaagg ccccggagga tctgggacac ctgaagaatg gcctgggcaa catactgagc     300
agtaataata atggcaccgg caatgggcac agtctgagcg aaaagtatgc ccatgaacag     360 gctccccctga ccggaggtta caagttgcca cctcgctcca gtgagtccga ggaatccgat     420
ttcgattccg acctcaatgg cggctcctcc gcggaatcca gctccagttg cggccttttc     480
ggctgtcggc ccaggtgggc cagaagattc gcgtccacgc acgtcttcat ggtggtcttc     540
ctgctggcct acatcctgca gggcatgtac atgacctact cgtctctgt gatcaccacc     600 attgagaagc tattccagat caagtcgaag accacgggaa ttctgctgag cgccagtgag     660
atgggtcaga tatgcacggc catgttgctg acctacttcg ccggcagagg acatcgtccg     720
agatggattg cctgcggcat ggtcctgttc tcaatcgccg ccttctcctg cgccctgccg     780
catttcatct tcggcgagca gctgatgcac tccagtgtaa ttctgcagca gacgcaggtc     840
tcccccccca ataattcctt ctcatcacac tggctgaatg ccagcagtga acaggttaat     900
cccaatttgt gcattttggg tggcaaccaa accattcgg gcagcgagtg caacgaggag     960
cgccagctgg aacaggcctc ccactctaag atcaccgtca tcgtgctgtg catcttcttt    1020
ggcagcctgc tcagctcggg cattggccag accgccgtgg ccacactggg catacccta c   1080
```

```
atcgatgaca atgtaggcag caagcagtcg cccatgtaca tggccgtcac cattggcatg      1140
aggatcctgg gaccggcatc cggtttcatt tttggcagct tctgcactcg ctggtatgtc      1200
aacttctcga atcccggctt cgacgccacg gatccgcgct ggattggcgc ctggtggctg      1260
gggcctgtgg ccattggcag cctcatgctg ctggcctcca tcgccatgtt ctcgtttccc      1320
aagcagttga gaggcaagca gaagccgccg gggcagacag caactccagc agctccagtt      1380
gagccggagg agaagcccaa gctaaaagat tttcccaaga cagtccgtcg ccagctgagc      1440
aacgacatcc tgatgttccg caccgcctcg tgcgtgttcc acctgctgcc catcgccggt      1500
ctctatacgt tcctgcccaa gtatctggag acgcagttcc ggctggccac ctatgatgcc      1560
aacatgatcg ccgccttctg tggcatcctg gtcatgggca taggtattgt catttccggg      1620
ctcttcatcc tgaagcgaaa gcccactgcc aggggcgtgg ccgcctggat cgcctttaca      1680
gccctcgtct actcggcggg catgatcatc ctgatgttca tcggctgcag catgaacgac      1740
tttgccggct acaagccaag cgatggcaac agtcccgcct tgatcgagcc cacgtgcagt      1800
gccgctctca actgtacctg tgataaggag aacttcgcgc ccatctgcgc cgacggcaaa      1860
atgtacatct cggcctgcca cgccggatgc agcagctcct cactgcggcc cagcgacaat      1920
cgcacactct actccgattg tgcttgcatt ccagatgctc cggaggcggt caacggttac      1980
tgtgataata actgcaagaa cttcatctac tttatactga tctttgccat ttgcgtattt      2040
atgcattcca cctccgaggt gggcagcatg ctgctcgtca tgcgctgcac acaccccaaa      2100
gataaggcca tggccatggg tgtgatacag tcggccatcg gcctgttcgg caacgttccc      2160
tgtcccatca tctacggcgc agtggtggac tccgcctgcc tcatctggaa gtcggtgtgc      2220
ggcaagcacg gcgcctgttc actctacgat gcggacactt tccggcaata tttcctagga      2280
atcacggctg gcattatgtt cctggcattc ctgatggatc tggtggtgtg cgcaaggcg       2340 catcgcattg acatcgcgcc cgaggatccg caggagggcg ggcccgcttc caacggaagg      2400
accttggagg tgtccgagtc caagcagccc atcaccccgg cgccggacac gacggtctag      2460
```

<210> SEQ ID NO 3
<211> LENGTH: 819
<212> TYPE: PRT
<213> ORGANISM: Drosophila melanogaster

<400> SEQUENCE: 3

```
Met Thr Lys Ser Asn Gly Asp Val Glu Ala Ala Gln Val Gln Ser
 1               5                  10                  15

Leu Gly Gly Lys Pro Ser Asn Gly His Gly Gln Leu Asn Gly Asn Gly
            20                  25                  30

Tyr His Gln Asn Gly Gly Arg Arg Asp Ser Ser Gln Ala Phe Thr Pro
        35                  40                  45

Leu Leu Ser Gln His Asn Asn Gly Thr Thr Asn Gly Glu Val Thr Thr
    50                  55                  60

Pro Pro Pro Ser Thr Val Leu Tyr Glu Ser Thr Pro Ser Asn Asn Asn
65                  70                  75                  80

Glu Trp Lys Ala Pro Glu Asp Leu Gly His Leu Lys Asn Gly Leu Gly
                85                  90                  95

Asn Ile Leu Ser Ser Asn Asn Gly Thr Gly Asn Gly His Ser Leu
                100                 105                 110

Ser Glu Lys Tyr Ala His Glu Gln Ala Pro Leu Thr Gly Gly Tyr Lys
            115                 120                 125

Leu Pro Pro Arg Ser Ser Glu Ser Glu Glu Ser Asp Phe Asp Ser Asp
```

```
            130                 135                 140
Leu Asn Gly Gly Ser Ser Ala Glu Ser Ser Ser Cys Gly Leu Phe
145                 150                 155                 160

Gly Cys Arg Pro Arg Trp Ala Arg Arg Phe Ala Ser Thr His Val Phe
                165                 170                 175

Met Val Val Phe Leu Leu Ala Tyr Ile Leu Gln Gly Met Tyr Met Thr
            180                 185                 190

Tyr Phe Val Ser Val Ile Thr Thr Ile Glu Lys Leu Phe Gln Ile Lys
        195                 200                 205

Ser Lys Thr Thr Gly Ile Leu Leu Ser Ala Ser Glu Met Gly Gln Ile
    210                 215                 220

Cys Thr Ala Met Leu Leu Thr Tyr Phe Ala Gly Arg Gly His Arg Pro
225                 230                 235                 240

Arg Trp Ile Ala Cys Gly Met Val Leu Phe Ser Ile Ala Ala Phe Ser
                245                 250                 255

Cys Ala Leu Pro His Phe Ile Phe Gly Glu Gln Leu Met His Ser Ser
            260                 265                 270

Val Ile Leu Gln Gln Thr Gln Val Ser Pro Pro Asn Asn Ser Phe Ser
        275                 280                 285

Ser His Trp Leu Asn Ala Ser Ser Glu Gln Val Asn Pro Asn Leu Cys
    290                 295                 300

Ile Leu Gly Gly Asn Gln Thr His Ser Gly Ser Glu Cys Asn Glu Glu
305                 310                 315                 320

Arg Gln Leu Glu Gln Ala Ser His Ser Lys Ile Thr Val Ile Val Leu
                325                 330                 335

Cys Ile Phe Phe Gly Ser Leu Leu Ser Ser Gly Ile Gly Gln Thr Ala
            340                 345                 350

Val Ala Thr Leu Gly Ile Pro Tyr Ile Asp Asp Asn Val Gly Ser Lys
        355                 360                 365

Gln Ser Pro Met Tyr Met Ala Val Thr Ile Gly Met Arg Ile Leu Gly
    370                 375                 380

Pro Ala Ser Gly Phe Ile Phe Gly Ser Phe Cys Thr Arg Trp Tyr Val
385                 390                 395                 400

Asn Phe Ser Asn Pro Gly Phe Asp Ala Thr Asp Pro Arg Trp Ile Gly
                405                 410                 415

Ala Trp Trp Leu Gly Pro Val Ala Ile Gly Ser Leu Met Leu Leu Ala
            420                 425                 430

Ser Ile Ala Met Phe Ser Phe Pro Lys Gln Leu Arg Gly Lys Gln Lys
        435                 440                 445

Pro Pro Gly Gln Thr Ala Thr Pro Ala Ala Pro Val Glu Pro Glu Glu
    450                 455                 460

Lys Pro Lys Leu Lys Asp Phe Pro Lys Thr Val Arg Arg Gln Leu Ser
465                 470                 475                 480

Asn Asp Ile Leu Met Phe Arg Thr Ala Ser Cys Val Phe His Leu Leu
                485                 490                 495

Pro Ile Ala Gly Leu Tyr Thr Phe Leu Pro Lys Tyr Leu Glu Thr Gln
            500                 505                 510

Phe Arg Leu Ala Thr Tyr Asp Ala Asn Met Ile Ala Ala Phe Cys Gly
        515                 520                 525

Ile Leu Val Met Gly Ile Gly Ile Val Ile Ser Gly Leu Phe Ile Leu
    530                 535                 540

Lys Arg Lys Pro Thr Ala Arg Gly Val Ala Ala Trp Ile Ala Phe Thr
545                 550                 555                 560
```

-continued

```
Ala Leu Val Tyr Ser Ala Gly Met Ile Ile Leu Met Phe Ile Gly Cys
                565                 570                 575
Ser Met Asn Asp Phe Ala Gly Tyr Lys Pro Ser Asp Gly Asn Ser Pro
            580                 585                 590
Ala Leu Ile Glu Pro Thr Cys Ser Ala Ala Leu Asn Cys Thr Cys Asp
        595                 600                 605
Lys Glu Asn Phe Ala Pro Ile Cys Ala Asp Gly Lys Met Tyr Ile Ser
    610                 615                 620
Ala Cys His Ala Gly Cys Ser Ser Ser Leu Arg Pro Ser Asp Asn
625                 630                 635                 640
Arg Thr Leu Tyr Ser Asp Cys Ala Cys Ile Pro Asp Ala Pro Glu Ala
                645                 650                 655
Val Asn Gly Tyr Cys Asp Asn Asn Cys Lys Asn Phe Ile Tyr Phe Ile
            660                 665                 670
Leu Ile Phe Ala Ile Cys Val Phe Met His Ser Thr Ser Glu Val Gly
        675                 680                 685
Ser Met Leu Leu Val Met Arg Cys Thr His Pro Lys Asp Lys Ala Met
    690                 695                 700
Ala Met Gly Val Ile Gln Ser Ala Ile Gly Leu Phe Gly Asn Val Pro
705                 710                 715                 720
Cys Pro Ile Ile Tyr Gly Ala Val Val Asp Ser Ala Cys Leu Ile Trp
                725                 730                 735
Lys Ser Val Cys Gly Lys His Gly Ala Cys Ser Leu Tyr Asp Ala Asp
                740                 745                 750
Thr Phe Arg Gln Tyr Phe Leu Gly Ile Thr Ala Gly Ile Met Phe Leu
                755                 760                 765
Ala Phe Leu Met Asp Leu Val Val Trp Arg Lys Ala His Arg Ile Asp
            770                 775                 780
Ile Ala Pro Glu Asp Pro Gln Glu Gly Gly Pro Ala Ser Asn Gly Arg
785                 790                 795                 800
Thr Leu Glu Val Ser Glu Ser Lys Gln Pro Ile Thr Pro Ala Pro Asp
                805                 810                 815
Thr Thr Val
```

METHODS FOR TARGETING MEMBRANE STEROID TRANSPORTERS

STATEMENT OF RIGHTS TO INVENTIONS MADE UNDER FEDERALLY SPONSORED RESEARCH

This invention was made with government support under Contract R00HD073239 awarded by the National Institutes of Health (NIH). The government has certain rights in the invention.

CROSS-REFERENCE TO RELATED APPLICATIONS

This application is a continuation application of U.S. patent application Ser. No. 15/883,809, filed Jan. 30, 2018, which claims priority to and the benefit of U.S. Provisional Patent Application No. 62/453,172, filed Feb. 1, 2017, the disclosures of each of which are incorporated herein by reference in their entireties.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 677032001001SEQLIST.txt, date recorded: Feb. 13, 2018, size: 15 KB).

FIELD

The present disclosure relates generally to chemical compounds that influence the cellular uptake of steroid hormones, and more specifically to screening methods for identifying chemical compounds that can influence the transport of steroid hormones across cell membranes by steroid hormone transporters.

BACKGROUND

Steroid hormones are a group of hormones that regulate diverse physiological and pathological processes, including immune response, energy homeostasis, sexual maturation and cancer progression. They enter target cells and bind to intracellular nuclear receptors, which then function as transcription factors and regulate gene expression in the nucleus. Steroid hormones are lipophilic, and are generally believed to enter cells by simple diffusion across the lipid bilayer.

There is interest in controlling the effects of steroid hormones, for example to regulate insect growth, to control inflammation, for hormone replacement therapy, or for the treatment of certain cancers. This is often done through the administration of synthetic or natural steroid hormones or steroid hormone antagonists to a subject. However, the administration of steroid hormones or steroid hormone antagonists often leads to unwanted side effects in the subject. Thus, what is desired in the art is methods to regulate the effect of steroid hormones and steroid hormone signaling in organisms, such as arthropods and humans.

BRIEF SUMMARY

In one aspect, provided is a method of identifying a compound that can modulate the transport of a steroid hormone across a phospholipid membrane, by:

providing a steroid hormone to an initial cell and a comparative cell in either the presence or absence of a candidate compound, wherein the initial cell expresses a steroid hormone transporter gene, and the expression of the steroid hormone transporter gene in the comparative cell is absent or lower than in the initial cell;

determining the amount of the steroid hormone that is transported across the phospholipid membrane of the initial cell and the comparative cell;

observing a difference between the amount of steroid hormone that is transported across the phospholipid membrane of the initial cell in the presence of the candidate compound compared to the absence of the candidate compound; and comparing the difference to the amount of steroid hormone that is transported across the phospholipid membrane of the comparative cell in the presence or absence of the candidate compound.

In some variations, the difference in the amount of steroid hormone transported across the phospholipid membrane is determined using a luciferase reporter assay.

In another aspect, provided is a method of identifying a compound that can affect the transcriptional activity of a steroid hormone nuclear receptor, by:

providing a steroid hormone to an initial cell and a comparative cell in either the presence or absence of a candidate compound, wherein the initial cell expresses a steroid hormone transporter gene, and the expression of the steroid hormone transporter gene in the comparative cell is absent or lower than in the initial cell;

determining the transcriptional activity of the steroid hormone nuclear receptor in the initial cell and the comparative cell;

observing a difference between the transcriptional activity in the initial cell in the presence of the candidate compound compared to the absence of the candidate compound; and comparing the difference to the transcriptional activity of the comparative cell in the presence or absence of the candidate compound.

In some variations, the difference in the transcriptional activity is determined using a luciferase reporter assay.

In certain variations, any of the preceding methods further include transfecting the initial cell, the comparative cell, or both with cDNA which includes the steroid hormone transporter gene. In some variations, the methods further include transfecting the initial cell, the comparative cell, or both with cDNA which includes the steroid hormone nuclear receptor gene.

In some variations, the steroid hormone transporter gene is of the solute carrier (SLC) family, for example of the solute carrier organic anion (SLCO) family. In certain variations, the gene encodes an organic anion-transporting polypeptide (OATP). In certain variations, the gene has the cDNA sequence of SEQ ID NO: 1.

In some variations, the steroid hormone is an ecdysteroid, estrogen, corticosteroid, progestogen, or androgen.

DESCRIPTION OF THE FIGURES

The present application can be understood by reference to the following description taken in conjunction with the accompanying drawing figures, in which like parts may be referred to by like numerals.

DETAILED DESCRIPTION

Figure 1A:
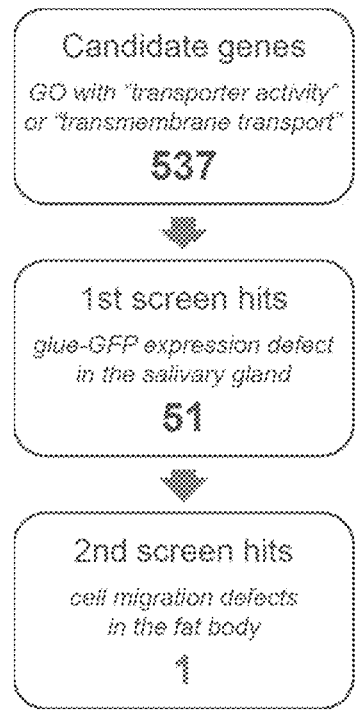
FIG. 1A is a scheme of in vivo RNAi screening for a gene encoding a membrane transporter for 20-hydroxyecdysone (20E).

The following description sets forth numerous exemplary configurations, methods, parameters, and the like. It should be recognized, however, that such description is not intended as a limitation on the scope of the present disclosure, but is instead provided as a description of exemplary embodiments.

In some aspects, provided herein are methods of identifying chemical compounds that can modulate the effect of steroid hormones in organisms. After crossing the phospholipid bilayer into the cell, certain steroid hormones bind to nuclear receptors, which in turn affect the expression of genes in the organism. It has been surprisingly found that instead of passively diffusing through the cell membrane, cellular uptake of certain steroid hormones is mediated by steroid hormone transporter polypeptides. Modulating the transport of a steroid hormone across a cell membrane by a polypeptide transporter may provide an alternative method of controlling the effect of the steroid hormones and steroid hormone signaling in an organism. Thus, in certain aspects, provided herein are methods of identifying chemical compounds that can modulate the transport of a steroid hormone across a phospholipid membrane by a steroid hormone transporter. In other aspects, provided herein are also methods of identifying chemical compounds that can modulate the transcriptional activity of a steroid hormone nuclear receptor, for example by modulating the transport of a steroid hormone across a membrane by a steroid hormone transporter. In yet other aspects, provided are compounds identified by the methods described herein, suitable for use as hormone agonists or hormone antagonists (e.g., in hormone therapy).

Methods of Screening Candidate Compounds

In some aspects, the methods described herein include screening candidate compounds to identify one or more compounds that affect the transport of a steroid hormone across a cell membrane by a steroid hormone transporter.

In some embodiments, the transport of the steroid hormone is evaluated in an initial cell in the presence and absence of a candidate compound. In certain embodiments, the initial cell expresses a steroid hormone transporter gene. For example, a compound may be identified if the transport of a steroid hormone by a steroid hormone transporter in an initial cell is increased or decreased in the presence of the compound, compared to transport in the absence of the compound.

Thus, in one embodiment, the screening method includes providing a steroid hormone to an initial cell in the presence and absence of a candidate compound, wherein the initial cell expresses a steroid hormone transporter gene; determining the amount of the steroid hormone that is transported across the phospholipid membrane of the initial cell in the presence and absence of the candidate compound; and observing a difference between the amount of steroid hormone that is transported across the phospholipid membrane of the initial cell in the presence of the candidate compound compared to the absence of the candidate compound.

In some variations, the transport of the steroid hormone in the initial cell is compared to the transport of the steroid hormone in a comparative cell. In some embodiments, both the initial cell and the comparative cell express the same steroid hormone transporter gene. In certain embodiments, the expression of the transporter gene in the comparative cell is lower than the expression of the transporter gene in the initial cell. In other embodiments, the initial cell expresses a steroid hormone transporter gene, while the comparative cell does not express the same transporter gene.

In some embodiments, a chemical compound is identified if the transport of a steroid hormone by a steroid hormone transporter in the presence of a candidate compound is different in an initial cell (e.g., higher or lower) than in a comparative cell.

In other embodiments, a chemical compound is identified if the presence of the compound has a greater effect on the transport by a steroid hormone transporter of a steroid hormone in an initial cell than in the comparative cell.

In some embodiments, the transport of the steroid hormone is evaluated by measuring the transcriptional activity of a steroid hormone nuclear receptor. For example, in some variations, the transcriptional activity of a steroid hormone nuclear receptor is increased or decreased in the presence of a candidate compound, compared to the transcriptional activity in the absence of the candidate compound.

Thus, in one embodiment, the screening method includes providing a steroid hormone to an initial cell in the presence and absence of a candidate compound, wherein the initial cell expresses a steroid hormone transporter gene; determining the transcriptional activity of the steroid hormone nuclear receptor in the presence and absence of the candidate compound; and observing a difference between the transcriptional activity of the initial cell in the presence of the candidate compound compared to the absence of the candidate compound.

Thus, in certain embodiments, the initial cell expresses a steroid hormone nuclear receptor gene. In some embodiments, the comparative cell expresses the same steroid hormone nuclear receptor gene. In still other embodiments, the initial cell and the comparative cell, if present, express the same steroid hormone transporter gene and the same steroid hormone nuclear receptor gene.

Steroid Hormone Transporter Gene

The initial cell or comparative cell used in the methods described herein may express any suitable steroid hormone transporter gene. In some embodiments, the initial cell and comparative cell both express the same steroid hormone transporter gene.

In some embodiments, the steroid hormone transporter gene is a mammalian gene, such as a human gene. In other embodiments, the steroid hormone transporter gene is an arthropod gene, such as a *D. melanogaster* gene. Thus, included herein are methods of screening candidate compounds to identify one or more compounds that affect the transport of a steroid hormone by a steroid hormone transporter into a mammalian or arthropod cell. In some embodiments, the mammal is a human.

In some embodiments, the steroid hormone transporter gene is of the solute carrier (SLC) family. In some embodiments, the steroid hormone transporter gene is of the solute carrier organic anion (SLCO) family. In still other embodiments, the steroid hormone transporter gene encodes an organic anion-transporting polypeptide (OATP). For example, in one embodiment, the steroid hormone transporter gene is Oatp74D. In one embodiment, the steroid hormone transporter gene is ecdysone importer (EcI). In one embodiment, the steroid hormone transporter gene Oatp74D is identical to the steroid hormone transporter gene ecdysone importer (EcI). In some embodiments, the steroid hormone transporter gene has the cDNA sequence of SEQ ID NO: 1. In one embodiment, the steroid hormone transporter gene has a cDNA sequence as shown in Table 1A.

TABLE 1A

| SEQ ID No | cDNA Sequence ecdysone importer ("EcI", Oatp74D) of *D. melanogaster* |
|---|---|
| 1 | TTACCGTGTGCGGACTGTGCCGACGGGCAGCGGAACTCAGGCGGTGCAACTTGA<br>GTGCTTGATAAATTTGTTGTATTGAAACCCAACCGCAAATACAATTTTCAATTGG<br>CTGAGTGCGTGTCTTCAACGCACAAACATACGAATATAGCATTTAATATTGTTCA<br>TTATGTGTGCAATTAAATAAAAAAAATTGTGTGTGAAATAACAGAAAAACGAGT<br>GCGGCGAACAGAGGCAGCAACAAATTAAACGCGTAAATTGCGTAGCAAATTCTG<br>AATGAAAAAATTCAACAAAACCAGAAAGCGAAACAGGAGCGATAAGCTTACCA<br>ACTAAAGAAACTCACGCCTAACAGAAATACACACCACTGCCATATTAAAGCAAA<br>GAATATAGAACTGTTTTACAGACCAGATCAACCAATCTACCTCGACTTCTGGGCC<br>AACAAGCAAAATAAAACTAAACTCAATGCCAGAACCCAATTTCCCGATAGGAAA<br>ATGGAACAGGCAATAAGCAAGACCCACATAGAGGAGATTAACTAAACGGATCCG<br>TTGAGATTACACAGTTGAGATCAATAAAACCCATTGAAGATCGATCAAACCATC<br>TAGTTTTTTAGAGTTCCATTAGAAGCCAAAATGACGAAGAGCAATGGCGATGTG<br>GAGGCGGCAGCCCAGGTGCAATCTCTGGGCGGAAAGCCCAGCAACGGACATGG<br>CCAGCTGAATGGGAATGGCTATCATCAGAACGGCGGACGCAGGGATTCCAGTCA<br>AGCCTTCACACCACTGCTGTCGCAGCACAATAATGGCACCACCAATGGCGAGGT<br>GACCACTCCGCCTCCGAGTACAGTGCTCTACGAGAGCACCCCGAGCAATAATAA<br>CGAGTGGAAGGCCCCGGAGGATCTGGGACACCTGAAGAATGGCCTGGGCAACAT<br>ACTGAGCAGTAATAATAATGGCACCGGCAATGGGCACAGTCTGAGCGAAAAGTA<br>TGCCCATGAACAGGCTCCCCTGACCGGAGGTTACAAGTTGCCACCTCGCTCCAGT<br>GAGTCCGAGGAATCCGATTTCGATTCCGACCTCAATGCCGGCTCCTCCGCGGAAT<br>CCAGCTCCAGTTGCGGCCTTTTCGGCTGTCGGCCCAGGTGGGCCAGAAGATTCGC<br>GTCCACGCACGTCTTCATGGTGGTCTTCCTGCTGGCCTACATCCTGCAGGGCATG<br>TACATGACCTACTTCGTCTCTGTGATCACCACCATTGAGAAGCTATTCCAGATCA<br>AGTCGAAGACCACGGGAATTCTGCTGAGCGCCAGTGAGATGGGTCAGATATGCA<br>CGGCCATGTTGCTGACCTACTTCGCCGGCAGAGGACATCGTCCGAGATGGATTGC<br>CTGCGGCATGGTCCTGTTCTCAATCGCCGCCTTCTCCTGCGCCCTGCCGCATTTCA<br>TCTTCGGCGAGCAGCTGATGCACTCCAGTGTAATTCTGCAGCAGACGCAGGTCTC<br>CCCCCCCAATAATTCCTTCTCATCACACTGGCTGAATGCCAGCAGTGAACAGGTT<br>AATCCCAATTTGTGCATTTTGGGTGGCAACCAAACCCATTCGGGCAGCGAGTGCA<br>ACGAGGAGCGCCAGCTGGAACAGGCCTCCCACTCTAAGATCACCGTCATCGTGC<br>TGTGCATCTTCTTTGGCAGCCTGCTCAGCTCGGGCATTGGCCAGACCGCCGTGGC<br>CACACTGGGCATACCCTACATCGATGACAATGTAGGCAGCAAGCAGTCGCCCAT<br>GTACATGGCCGTCACCATTGGCATGAGGATCCTGGGACCGGCATCCGGTTTCATT<br>TTTGGCAGCTTCTGCACTCGCTGGTATGTCAACTTCTCGAATCCCGGCTTCGACG<br>CCACGGATCCGCGCTGGATTGCGCCTGGTGGCTGGGGCCTGTGGCCATTGGCA<br>GCCTCATGCTGCTGGCCTCCATCGCCATGTTCTCGTTTCCCAAGCAGTTGAGAGG<br>CAAGCAGAAGCCGCCGGGGCAGACAGCAACTCCAGCAGCTCCAGTTGAGCCGG<br>AGGAGAAGCCCAAGCTAAAAGATTTTCCCAAGACAGTCCGTCGCCAGCTGAGCA<br>ACGACATCCTGATGTTCCGCACCGCCTCGTGCGTGTTCCACCTGCTGCCCATCGC<br>CGGTCTCTATACGTTCCTGCCCAAGTATCTGGAGACGCAGTTCCGGCTGGCCACC<br>TATGATGCCAACATGATCGCCGCCTTCTGTGGCATCCTGGTCATGGGCATAGGTA<br>TTGTCATTTCCGGGCTCTTCATCCTGAAGCGAAAGCCCACTGCCAGGGGCGTGGC |

TABLE 1A-continued

| SEQ ID No | cDNA Sequence ecdysone importer ("EcI", Oatp74D) of *D. melanogaster* |
|---|---|
| | CGCCTGGATCGCCTTTACAGCCCTCGTCTACTCGGCGGGCATGATCATCCTGATG<br>TTCATCGGCTGCAGCATGAACGACTTTGCCGGCTACAAGCCAAGCGATGGCAAC<br>AGTCCCGCCTTGATCGAGCCCACGTGCAGTGCCGCTCTCAACTGTACCTGTGATA<br>AGGAGAACTTCGCGCCCATCTGCGCCGACGGCAAAATGTACATCTCGGCCTGCC<br>ACGCCGGATGCAGCAGCTCCTCACTGCGGCCCAGCGACAATCGCACACTCTACT<br>CCGATTGTGCTTGCATTCCAGATGCTCCGGAGGCGGTCAACGGTTACTGTGATAA<br>TAACTGCAAGAACTTCATCTACTTTATACTGATCTTTGCCATTTGCGTATTTATGC<br>ATTCCACCTCCGAGGTGGGCAGCATGCTGCTCGTCATGCGCTGCACACACCCAA<br>AGATAAGGCCATGGCCATGGGTGTGATACAGTCGGCCATCGGCCTGTTCGGCAA<br>CGTTCCCTGTCCCATCATCTACGGCGCAGTGGTGGACTCCGCCTGCCTCATCTGG<br>AAGTCGGTGTGCGGCAAGCACGGCGCCTGTTCACTCTACGATGCGGACACTTTCC<br>GGCAATATTTCCTAGGAATCACGGCTGGCATTATGTTCCTGGCATTCCTGATGGA<br>TCTGGTGGTGTGGCGCAAGGCGCATCGCATTGACATCGCGCCCGAGGATCCGCA<br>GGAGGGCGGGCCCGCTTCCAACGGAAGGACCTTGGAGGTGTCCGAGTCCAAGCA<br>GCCCATCACCCCGGCGCCGGACACGACGGTCTAGGAGGAGCGGGTCGGCGACGA<br>GCCTTGCACAAGCTGCAGGATTTCCAATAAACGTTTACCTTAATTGTTAATTAGT<br>TATCATTTGTCTAGTTTGTTAGCCTAGTGCAAGAGTTATGTATTTAGTTAAGTGGC<br>ATCTTCGAGCGTCGGGAGACCTCATTCAAATCCACATTAGAACGCGCTCGTCCAG<br>CTCCCGCTCCCGATCCTGCTCCAAATCCCAGCACCATATTCTACATGAAGCCCAT<br>GGATTGCGATTTGAATCCTTGTAAATCTCAACGCGAAACAATGAAATGAAATTCT<br>AGACATTATCTAACGTCATGCATGAGCGTAGTTAATCGACGAGCTAATACTACA<br>AACTGATCGACAATTGTGCAAAGTGCAAGAAAATTTATGAATCCTTATGTGTAA<br>ACTATATGTAACAGTTATATCGCGATGTATGTAATCTATAATTAATATATTAGAC<br>ATACACTTACATGTATGTATGTAATTGCAACCTATCTGTGGTAGTTAAATTTTAGT<br>TAAAATTCAAATTAATTGTCTAAGTTTGTCATACAACAAATATATACGAAAAGAA<br>ATTAAATGGAAAACTATATACAAGTAAAAAAAAAAAAAAAAAAA |

In some embodiments, the steroid hormone transporter gene has the coding sequence of SEQ ID NO: 2. In one embodiment, the steroid hormone transporter gene has a coding sequence as shown in Table 1B.

TABLE 1B

| SEQ ID No | Coding Sequence ecdysone importer ("EcI", Oatp74D) of *D. melanogaster* |
|---|---|
| 2 | ATGACGAAGAGCAATGGCGATGTGGAGGCGGCAGCCCAGGTGCAATCTCTGGGC<br>GGAAAGCCCAGCAACGGACATGGCCAGCTGAATGGGAATGGCTATCATCAGAAC<br>GGCGGACGCAGGGATTCCAGTCAAGCCTTCACACCACTGCTGTCGCAGCACAAT<br>AATGGCACCACCAATGGCGAGGTGACCACTCCGCCTCCGAGTACAGTGCTCTAC<br>GAGAGCACCCCGAGCAATAATAACGAGTGGAAGGCCCCGGAGGATCTGGGACA<br>CCTGAAGAATGGCCTGGGCAACATACTGAGCAGTAATAATAATGGCACCGGCAA<br>TGGGCACAGTCTGAGCGAAAAGTATGCCCATGAACAGGCTCCCCTGACCGGAGG<br>TTACAAGTTGCCACCTCGCTCCAGTGAGTCCGAGGAATCCGATTTCGATTCCGAC<br>CTCAATGCGGCTCCTCCGCGGAATCCAGCTCCAGTTGCGGCCTTTTCGGCTGTC<br>GGCCCAGGTGGGCCAGAAGATTCGCGTCCACGCACGTCTTCATGGTGGTCTTCCT<br>GCTGGCCTACATCCTGCAGGGCATGTACATGACCTACTTCGTCTCTGTGATCACC<br>ACCATTGAGAAGCTATTCCAGATCAAGTCGAAGACCACGGGAATTCTGCTGAGC<br>GCCAGTGAGATGGGTCAGATATGCACGGCCATGTTGCTGACCTACTTCGCCGGC<br>AGAGGACATCGTCCGAGATGGATTGCCTGCGGCATGGTCCTGTTCTCAATCGCCG<br>CCTTCTCCTGCGCCCTGCCGCATTTCATCTTCGGCGAGCAGCTGATGCACTCCAG<br>TGTAATTCTGCAGCAGACGCAGGTCTCCCCCCCCAATAATTCCTTCTCATCACAC<br>TGGCTGAATGCCAGCAGTGAACAGGTTAATCCCAATTTGTGCATTTTGGGTGGCA<br>ACCAAACCCATTCGGGCAGCGAGTGCAACGAGGAGCGCCAGCTGGAACAGGCCT<br>CCCACTCTAAGATCACCGTCATCGTCTGTGCATCTTCTTTGGCAGCCTGCTCAG<br>CTCGGGCATTGGCCAGACCGCCGTGGCCACACTGGGCATACCCTACATCGATGA<br>CAATGTAGGCAGCAAGCAGTCGCCCATGTACATGGCCGTCACCATTGGCATGAG<br>GATCCTGGGACCGGCATCCGGTTTCATTTTTGGCAGCTTCTGCACTCGCTGGTAT<br>GTCAACTTCTCGAATCCCGGCTTCGACGCCACGGATCCGCGCTGGATTGGCGCCT<br>GGTGGCTGGGGCCTGTGGCCATTGGCAGCCTCATGCTGCTGGCCTCCATCGCCAT<br>GTTCTCGTTTCCCAAGCAGTTGAGAGGCAAGCAGAAGCCGCCGGGGCAGACAGC<br>AACTCCAGCAGCTCCAGTTGAGCCGGAGGAGAAGCCCAAGCTAAAAGATTTTCC<br>CAAGACAGTCCGTCGCCAGCTGAGCAACGACATCCTGATGTTCCGCACCGCCTC<br>GTGCGTGTTCCACCTGCTGCCCATCGCCGGTCTCTATACGTTCCTGCCCAAGTATC<br>TGGAGACGCAGTTCCGGCTGGCCACCTATGATGCCAACATGATCGCCGCCTTCTG<br>TGGCATCCTGGTCATGGGCATAGGTATTGTCATTTCCGGGCTCTTCATCCTGAAG<br>CGAAAGCCCACTGCCAGGGCGTGGCCGCCTGGATCGCCTTTACAGCCCTCGTCT<br>ACTCGGCGGGCATGATCATCCTGATGTTCATCGGCTGCAGCATGAACGACTTTGC<br>CGGCTACAAGCCAAGCGATGGCAACAGTCCCGCCTTGATCGAGCCCACGTGCAG<br>TGCCGCTCTCAACTGTACCTGTGATAAGGAGAACTTCGCGCCCATCTGCGCCGAC<br>GGCAAAATGTACATCTCGGCCTGCCACGCCGGATGCAGCAGCTCCTCACTGCGG<br>CCCAGCGACAATCGCACACTCTACTCCGATTGTGCTTGCATTCCAGATGCTCCGG<br>AGGCGGTCAACGGTTACTGTGATAATAACTGCAAGAACTTCATCTACTTTATACT<br>GATCTTTGCCATTTGCGTATTTATGCATTCCACCTCCGAGGTGGGCAGCATGCTG<br>CTCGTCATGCGCTGCACACACCCCAAAGATAAGGCCATGGCCATGGGTGTGATA |

TABLE 1B-continued

| SEQ<br>ID No | Coding Sequence<br>ecdysone importer ("EcI", Oatp74D) of *D. melanogaster* |
|---|---|
| | CAGTCGGCCATCGGCCTGTTCGGCAACGTTCCCTGTCCCATCATCTACGGCGCAG<br>TGGTGGACTCCGCCTGCCTCATCTGGAAGTCGGTGTGCGGCAAGCACGGCGCCT<br>GTTCACTCTACGATGCGGACACTTTCCGGCAATATTTCCTAGGAATCACGGCTGG<br>CATTATGTTCCTGGCATTCCTGATGGATCTGGTGGTGTGGCGCAAGGCGCATCGC<br>ATTGACATCGCGCCCGAGGATCCGCAGGAGGGCGGGCCCGCTTCCAACGGAAGG<br>ACCTTGGAGGTGTCCGAGTCCAAGCAGCCCATCACCCCGGCGCCGGACACGACG<br>GTCTAG |

In some embodiments, the steroid hormone transporter gene has the amino acid sequence of SEQ ID NO: 3. In one embodiment, the steroid hormone transporter gene has an amino acid sequence as shown in Table 1C.

TABLE 1C

| SEQ<br>ID No | Amino Acid Sequence<br>ecdysone importer ("EcI", Oatp74D) of *D. melanogaster* |
|---|---|
| 3 | MTKSNGDVEAAAQVQSLGGKPSNGHGQLNGNGYHQNGGRRDSSQAFTPLLSQHNN<br>GTTNGEVTTPPPSTVLYESTPSNNNEWKAPEDLGHLKNGLGNILSSNNNGTGNGHSL<br>SEKYAHEQAPLTGGYKLPPRSSESEESDFDSDLNGGSSAESSSSCGLFGCRPRWARRF<br>ASTHVFMVVFLLAYILQGMYMTYFVSVITTIEKLFQIKSKTTGILLSASEMGQICTAM<br>LLTYFAGRGHRPRWIACGMVLFSIAAFSCALPHFIFGEQLMHSSVILQQTQVSPPNNS<br>FSSHWLNASSEQVNPNLCILGGNQTHSGSECNEERQLEQASHSKITVIVLCIFFGSLLS<br>SGIGQTAVATLGIPYIDDNVGSKQSPMYMAVTIGMRILGPASGFIFGSFCTRWYVNFS<br>NPGFDATDPRWIGAWWLGPVAIGSLMLLASIAMFSFPKQLRGKQKPPGQTATPAAP<br>VEPEEKPKLKDFPKTVRRQLSNDILMFRTASCVFHLLPIAGLYTFLPKYLETQFRLAT<br>YDANMIAAFCGILVMGIGIVISGLFILKRKPTARGVAAWIAFTALVYSAGMIILMFIGC<br>SMNDFAGYKPSDGNSPALIEPTCSAALNCTCDKENFAPICADGKMYISACHAGCSSS<br>SLRPSDNRTLYSDCACIPDAPEAVNGYCDNNCKNFIYFILIFAICVFMHSTSEVGSMLL<br>VMRCTHPKDKAMAMGVIQSAIGLFGNVPCPIIYGAVVDSACLIWKSVCGKHGACSL<br>YDADTFRQYFLGITAGIMFLAFLMDLVVWRKAHRIDIAPEDPQEGGPASNGRTLEVS<br>ESKQPITPAPDTTV |

In some embodiments, the steroid hormone transporter gene is introduced into the initial cell, or the comparative cell, or both. The gene may be introduced using any suitable methods, such as transfection. In some embodiments, the initial cell is transfected with cDNA encoding the steroid hormone transporter gene. In some embodiments, the comparative cell is transfected with cDNA encoding the steroid hormone transporter gene.

In some embodiments, the comparative cell has lower expression or no expression of the steroid hormone transporter gene. In one embodiment, expression of the transporter gene in the comparative cell is decreased through RNA interference (RNAi).

Steroid Hormone Nuclear Receptor

In some variations, the methods include measuring the transcriptional activity of a steroid hormone nuclear receptor. Thus, in certain embodiments, the initial cell, the comparative cell (if present), or both cells express a steroid hormone nuclear receptor gene. In some embodiments, the steroid hormone nuclear receptor gene encodes a receptor that binds to one or more ecdysteroids (such as 20E), estrogens (such as estradiol), corticosteroids (such as cortisol), progestogens (such as progesterone), or androgens (such as testosterone), or any combinations thereof. In some embodiments, the steroid hormone nuclear receptor gene encodes a receptor that binds to 20-hydroxyecdysone, estradiol, cortisol, progesterone, or testosterone.

In one embodiment, the steroid hormone nuclear receptor gene is ecdysone receptor (EcR), estrogen receptor 1 (ESR1 or NR3A1), estrogen receptor 2 (ESR2 or NR3A2), glucocorticoid receptor (GR or NR3C1), progesterone receptor (PR or NR3C3) or androgen receptor (AR or NR3C4). In one embodiment, the steroid hormone nuclear receptor gene is ecdysone receptor (EcR).

In some embodiments, the steroid hormone nuclear receptor gene is introduced into the initial cell, or the comparative cell, or both. The gene may be introduced using any suitable methods, such as transfection. In some embodiments, the initial cell is transfected with cDNA encoding the steroid hormone nuclear receptor gene. In some embodiments, the comparative cell is transfected with cDNA encoding the steroid hormone nuclear receptor gene.

In some embodiments, the comparative cell has lower expression or no expression of the steroid hormone nuclear receptor gene. In one embodiment, expression of the nuclear receptor gene in the comparative cell is decreased through RNA interference (RNAi).

Transcriptional Activity

Figure 5A:
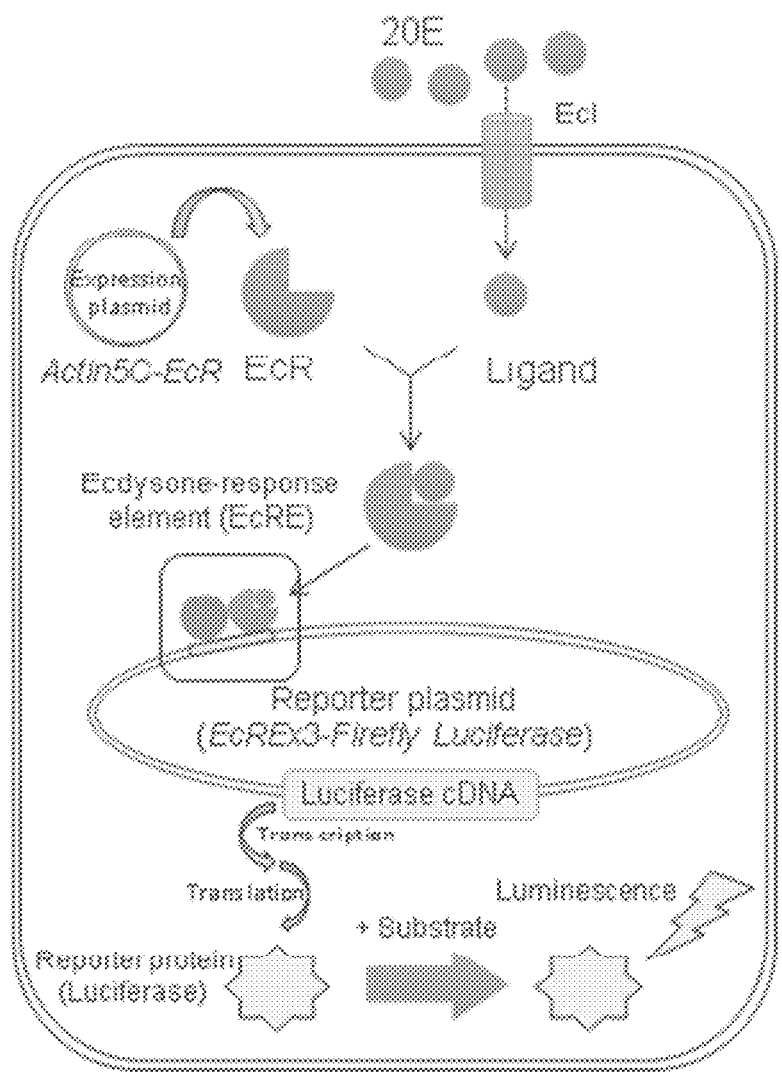
FIG. 5A depicts a schematic of a luciferase reporter assay in a cell derived from an arthropod cell line, for determining transport of 20E by the membrane steroid hormone transporter encoded by ecdysone importer (EcI).
Figure 5B:
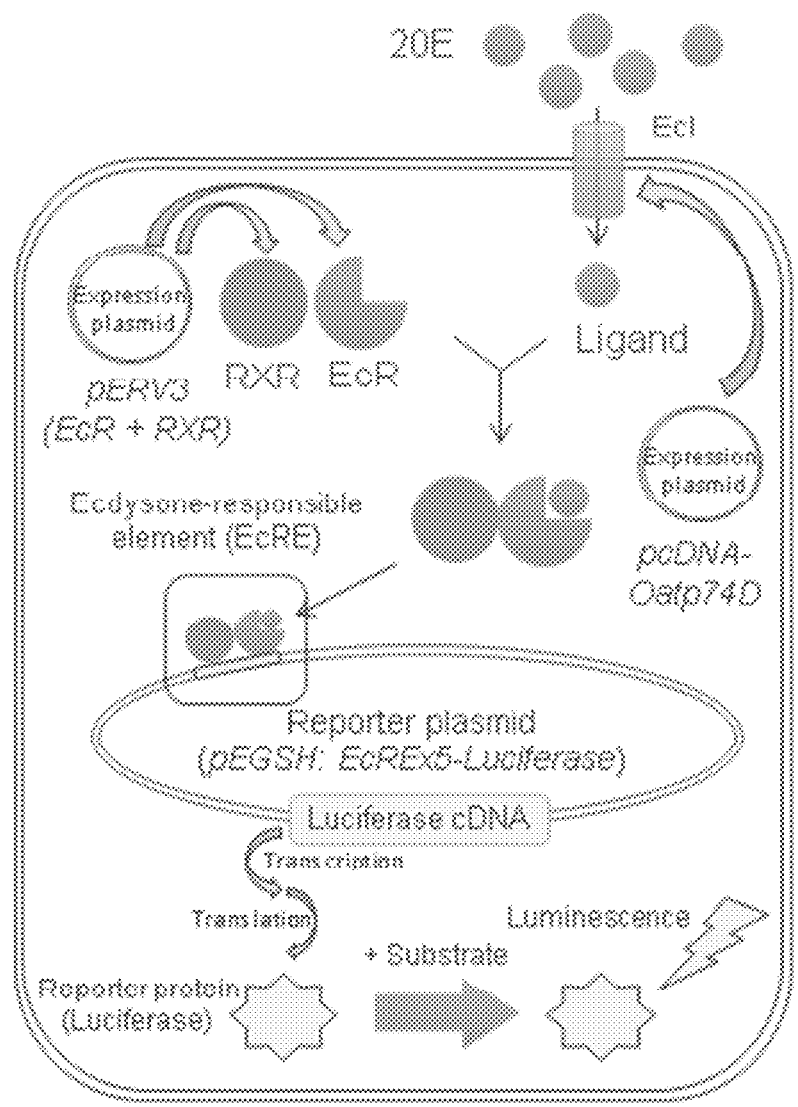
FIG. 5B depicts a schematic of a luciferase reporter assay in a cell derived from a mammalian cell line, for determining transport of 20E by the membrane steroid hormone transporter encoded by ecdysone importer (EcI).

As described above, in some embodiments, the transcriptional activity of a steroid hormone nuclear receptor is used to evaluate the transport of a steroid hormone across the cell membrane of an initial cell, or a comparative cell. In some variations, the luciferase reporter assay is used to measure the transcriptional activity of the steroid hormone nuclear receptor. For example, with reference to FIG. 5A and FIG. 5B, depicted are schemes showing the use of a luciferase reporter assay in an S2 cell (FIG. 5A) or in a HEK cell (FIG. 5B) to evaluate the transcriptional activity of the nuclear receptor encoded by the gene ecdysone receptor (EcR).

Cell Types

The screening methods described herein may be carried out using any appropriate type of cell or cell line. In some embodiments, a heterologous expression system is used.

In certain embodiments, one or more cells or cell culture lines derived from an animal are used. In some embodiments, the one or more cells or cell culture lines are derived from a mammal, an arthropod, or an amphibian. For example, in some variations, the screening methods include the use of one or more cells or cell culture lines derived from humans, an organism of the genus *Drosophila*, or an organism of the genus *Xenopus*. In some embodiments, the methods include the use of human embryonic kidney (HEK) cells, CHO cells, HeLa cells, cells from *D. melanogaster* (such as Schneider 2 (S2) cells), or *Xenopus* oocytes. Thus, for example, in some embodiments the initial cell is a HEK cell, CHO cell, HeLa cell, S2 cell, or *Xenopus* oocyte. In some embodiments, the comparative cell is a HEK cell, CHO cell, HeLa cell, S2 cell, or *Xenopus* oocyte. In some embodiments, the initial cell and the comparative cell are the same type of cell. In some embodiments, the initial cell is from *D. melanogaster*. In some embodiments, the comparative cell is from *D. melanogaster*.

In some embodiments, the initial cell and the comparative cell are the same type of cell, but differ in expression of the steroid hormone transporter gene. In some embodiments, the initial cell and the comparative cell are cells or cell culture lines derived from the same species (for example, cells or cell culture lines derived from humans, an organism of the genus *Drosophila*, or an organism of the genus *Xenopus*), and the comparative cell has lower expression of the steroid hormone transporter gene than the initial cell. In some embodiments, the initial cell and the comparative cell are cells or cell culture lines derived from the same species (for example, cells or cell culture lines derived from humans, an organism of the genus *Drosophila*, or an organism of the genus *Xenopus*), the initial cell expresses the steroid hormone transporter gene, and the comparative cell has no expression of the steroid hormone transporter gene. In some embodiments, the initial cell and the comparative cell are derived from the same cells or cell culture line (for example, human embryonic kidney (HEK) cells, CHO cells, HeLa cells, cells from *D. melanogaster* (such as Schneider 2 (S2) cells), or *Xenopus* oocytes), and the comparative cell has lower expression of the steroid hormone transporter gene than the initial cell. In some embodiments, the initial cell and the comparative cell are derived from the same cell or cell culture line (for example, human embryonic kidney (HEK) cells, CHO cells, HeLa cells, cells from *D. melanogaster* (such as Schneider 2 (S2) cells), or *Xenopus* oocytes), the initial cell expresses the steroid hormone transporter gene, and the comparative cell has no expression of the steroid hormone transporter gene.

Steroid Hormones

The methods described herein may be used to evaluate the transport of any suitable steroid hormone. In some embodiments, the steroid is an ecdysteroid (such as 20E), estrogen (such as estradiol), corticosteroid (such as cortisol), progestogen (such as progesterone), or androgen (such as testosterone). In some embodiments, the steroid hormone is 20-hydroxyecdysone, estradiol, cortisol, progesterone or testosterone.

EXAMPLES

The following Examples are merely illustrative and are not meant to limit any aspects of the present disclosure in any way.

Example 1

Identification of Ecdysone Importer (EcI)

The gene ecdysone importer was identified using an in vivo RNAi screen (FIG. 1A).

537 candidate genes were selected based on "gene ontology" (GO) terms, and screened for their knockdown effects on ecdysone-dependent glue-GFP expression in the salivary gland (SG) of *D. melanogaster*. From this screen, 51 RNAi lines were found to diminish GFP signal in the SG. These were further tested for their effect on ecdysone-dependent cell migration in the fat body (FB) of flies, which yielded a single hit, Oatp74D (CG7571). This gene was renamed ecdysone importer (EcI). The 537 candidate genes and the screening outcome are shown in Table 2.

TABLE 2

| # | Symbol | Stock Center | RNAi Stock ID # | glue-GFP expression defect* | fat body cell migration defect** |
|---|---|---|---|---|---|
| 459 | Oatp74D | VDRC | 37295 | YES | YES |
| 7 | Ant2 | VDRC | 102533 | YES | NO |
| 40 | CG10804 | BDSC | 29599 | YES | NO |
| 43 | CG10920 | BDSC | 44650 | YES | NO |
| 84 | CG13743 | VDRC | 40974 | YES | NO |
| 166 | CG31229 | VDRC | 106764 | YES | NO |
| 243 | CG4797 | VDRC | 10598 | YES | NO |
| 277 | CG6356 | BDSC | 28745 | YES | NO |
| 361 | Cog3 | VDRC | 108574 | YES | NO |
| 385 | emb | BDSC | 34021 | YES | NO |
| 390 | exo70 | BDSC | 55234 | YES | NO |
| 392 | fabp/sea | BDSC | 34685 | YES | NO |
| 437 | msk | BDSC | 33626 | YES | NO |
| 483 | Rph | BDSC | 25950 | YES | NO |
| 506 | Surf6 | BDSC | 34563 | YES | NO |
| 527 | vib | VDRC | 26848 | YES | NO |
| 395 | foi | BDSC | 55281 | YES | NO |
| 528 | Vmat | BDSC | 44471 | YES | NO |
| 73 | CG12858 | BDSC | 43284 | YES | NO |
| 190 | CG32091 | BDSC | 57783 | YES | NO |
| 8 | AP-1gamma | BDSC | 27533 | YES | NO |
| 520 | Ucp4B | VDRC | 33130 | YES | NO |
| 27 | cdm | BDSC | 44551 | YES | NO |
| 176 | CG3168 | BDSC | 29301 | YES | NO |
| 258 | CG5549 | VDRC | 8222 | YES | NO |
| 326 | CG8713 | BDSC | 25853 | YES | NO |
| 118 | CG1703 | VDRC | 105998 | YES | NO |
| 10 | AP-2sigma | BDSC | 27322 | YES | NO |
| 59 | CG11779 | BDSC | 43155 | YES | NO |
| 278 | CG6404 | VDRC | 108091 | YES | NO |
| 219 | CG42260 | BDSC | 26723 | YES | NO |
| 170 | CG3149 | BDSC | 53324 | YES | NO |
| 174 | CG3164 | BDSC | 57478 | YES | NO |
| 391 | Exp6 | VDRC | 34737 | YES | NO |
| 151 | CG2930 | BDSC | 54827 | YES | NO |
| 431 | mge | BDSC | 57430 | YES | NO |
| 209 | CG34120 | BDSC | 34596 | YES | NO |
| 269 | CG6006 | BDSC | 55282 | YES | NO |
| 462 | Orct | BDSC | 60125 | YES | NO |
| 126 | CG17646 | BDSC | 26008 | YES | NO |
| 364 | cpx | BDSC | 42017 | YES | NO |
| 432 | mnd | VDRC | 110217 | YES | NO |
| 41 | CG10864 | BDSC | 25878 | YES | NO |
| 242 | CG4743 | BDSC | 56025 | YES | NO |
| 294 | CG7309 | BDSC | 44653 | YES | NO |
| 367 | CtrlA | BDSC | 44000 | YES | NO |
| 393 | Fatp | BDSC | 55919 | YES | NO |
| 398 | g | VDRC | 41369 | YES | NO |
| 56 | CG11659 | BDSC | 55268 | YES | NO |
| 363 | Cpr47Eg | BDSC | 56004 | YES | NO |
| 470 | Pen | BDSC | 27692 | YES | NO |
| 421 | Mdr49 | BDSC | 32405 | NO | ND |
| 1 | ABCB7 | BDSC | 51696 | NO | ND |
| 2 | AChT | BDSC | 27684 | NO | ND |
| 3 | Afti | VDRC | 104750 | NO | ND |
| 4 | alpha-Adaptin | VDRC | 15565 | NO | ND |
| 5 | alphaKap4 | VDRC | 108143 | NO | ND |
| 6 | Ank2 | BDSC | 33414 | NO | ND |
| 9 | AP-1sigma | BDSC | 40895 | NO | ND |
| 11 | AP-47 | VDRC | 24017 | NO | ND |
| 12 | AP-50 | VDRC | 103390 | NO | ND |
| 13 | AQP | BDSC | 51504 | NO | ND |

TABLE 2-continued

| # | Symbol | Stock Center | RNAi Stock ID # | glue-GFP expression defect* | fat body cell migration defect** |
|---|---|---|---|---|---|
| 14 | aralar1 | BDSC | 56884 | NO | ND |
| 15 | Atet | BDSC | 57796 | NO | ND |
| 16 | ATP7 | BDSC | 31083 | NO | ND |
| 17 | Atpalpha | BDSC | 32913 | NO | ND |
| 18 | att-ORFA | VDRC | 50707 | NO | ND |
| 19 | bai | VDRC | 100612 | NO | ND |
| 20 | bap | BDSC | 27061 | NO | ND |
| 21 | bdg | VDRC | 110054 | NO | ND |
| 22 | blot | VDRC | 101083 | NO | ND |
| 23 | Bmcp | BDSC | 37498 | NO | ND |
| 24 | btsz | BDSC | 40898 | NO | ND |
| 25 | bw | VDRC | 101584 | NO | ND |
| 26 | Catsup | BDSC | 55396 | NO | ND |
| 28 | cert | BDSC | 60080 | NO | ND |
| 29 | CG10006 | VDRC | 101031 | NO | ND |
| 30 | CG10019 | VDRC | 7292 | NO | ND |
| 31 | CG10026 | VDRC | 107452 | NO | ND |
| 32 | CG10226 | VDRC | 108196 | NO | ND |
| 33 | CG10237 | VDRC | 108388 | NO | ND |
| 34 | CG10300 | VDRC | 109472 | NO | ND |
| 35 | CG10413 | BDSC | 38364 | NO | ND |
| 36 | CG10444 | VDRC | 107008 | NO | ND |
| 37 | CG10486 | VDRC | 107903 | NO | ND |
| 38 | CG10505 | BDSC | 38317 | NO | ND |
| 39 | CG10657 | VDRC | 103376 | NO | ND |
| 42 | CG1090 | BDSC | 25806 | NO | ND |
| 44 | CG10950 | VDRC | 41462 | NO | ND |
| 45 | CG10960 | BDSC | 34598 | NO | ND |
| 46 | CG11069 | VDRC | 101080 | NO | ND |
| 47 | CG11147 | BDSC | 57741 | NO | ND |
| 48 | CG11163 | VDRC | 107931 | NO | ND |
| 49 | CG11262 | VDRC | 105920 | NO | ND |
| 50 | CG11374 | VDRC | 15562 | NO | ND |
| 51 | CG1139 | VDRC | 102363 | NO | ND |
| 52 | CG11391 | BDSC | 56947 | NO | ND |
| 53 | CG11407 | VDRC | 107610 | NO | ND |
| 54 | CG11537 | BDSC | 43180 | NO | ND |
| 55 | CG11655 | VDRC | 9131 | NO | ND |
| 57 | CG11665 | VDRC | 52902 | NO | ND |
| 58 | CG11739 | BDSC | 38230 | NO | ND |
| 60 | CG11897 | BDSC | 38318 | NO | ND |
| 61 | CG11898 | VDRC | 100660 | NO | ND |
| 62 | CG12004 | VDRC | 101732 | NO | ND |
| 63 | CG12027 | VDRC | 108418 | NO | ND |
| 64 | CG12061 | BDSC | 26248 | NO | ND |
| 65 | CG1213 | VDRC | 6487 | NO | ND |
| 66 | CG12194 | VDRC | 109287 | NO | ND |
| 67 | CG12201 | VDRC | 109013 | NO | ND |
| 68 | CG12376 | VDRC | 22882 | NO | ND |
| 69 | CG12490 | BDSC | 44511 | NO | ND |
| 70 | CG12531 | VDRC | 105771 | NO | ND |
| 71 | CG12773 | VDRC | 108667 | NO | ND |
| 72 | CG12783 | BDSC | 27678 | NO | ND |
| 74 | CG12866 | BDSC | 57427 | NO | ND |
| 75 | CG12926 | VDRC | 109580 | NO | ND |
| 76 | CG12943 | BDSC | 56990 | NO | ND |
| 77 | CG13189 | VDRC | 105650 | NO | ND |
| 78 | CG13223 | VDRC | 1683 | NO | ND |
| 79 | CG13248 | BDSC | 28761 | NO | ND |
| 80 | CG13384 | BDSC | 41703 | NO | ND |
| 81 | CG13426 | VDRC | 107528 | NO | ND |
| 82 | CG1358 | VDRC | 101453 | NO | ND |
| 83 | CG13646 | BDSC | 53701 | NO | ND |
| 85 | CG13793 | VDRC | 50167 | NO | ND |
| 86 | CG13794 | VDRC | 102583 | NO | ND |
| 87 | CG13795 | VDRC | 102250 | NO | ND |
| 88 | CG13796 | BDSC | 57251 | NO | ND |
| 89 | CG13801 | VDRC | 104206 | NO | ND |
| 90 | CG13893 | VDRC | 108011 | NO | ND |
| 91 | CG13907 | VDRC | 110059 | NO | ND |
| 92 | CG14040 | VDRC | 110668 | NO | ND |
| 93 | CG14160 | VDRC | 104744 | NO | ND |
| 94 | CG14511 | VDRC | 107875 | NO | ND |
| 95 | CG14605 | VDRC | 105310 | NO | ND |
| 96 | CG14606 | VDRC | 100903 | NO | ND |
| 97 | CG14691 | BDSC | 31986 | NO | ND |
| 98 | CG14743 | VDRC | 105880 | NO | ND |
| 99 | CG14744 | VDRC | 108697 | NO | ND |
| 100 | CG14767 | BDSC | 34679 | NO | ND |
| 101 | CG14855 | BDSC | 57569 | NO | ND |
| 102 | CG14856 | VDRC | 101004 | NO | ND |
| 103 | CG1494 | BDSC | 57777 | NO | ND |
| 104 | CG15096 | VDRC | 107275 | NO | ND |
| 105 | CG15221 | BDSC | 31888 | NO | ND |
| 106 | CG15279 | BDSC | 50583 | NO | ND |
| 107 | CG15406 | VDRC | 105077 | NO | ND |
| 108 | CG15408 | BDSC | 58239 | NO | ND |
| 109 | CG15553 | BDSC | 28016 | NO | ND |
| 110 | CG15828 | VDRC | 51937 | NO | ND |
| 111 | CG15890 | BDSC | 28768 | NO | ND |
| 112 | CG1607 | BDSC | 57797 | NO | ND |
| 113 | CG1628 | BDSC | 54464 | NO | ND |
| 114 | CG16700 | VDRC | 110058 | NO | ND |
| 115 | CG16727 | BDSC | 57434 | NO | ND |
| 116 | CG1688 | BDSC | 25809 | NO | ND |
| 117 | CG1698 | VDRC | 101947 | NO | ND |
| 119 | CG17119 | BDSC | 40823 | NO | ND |
| 120 | CG17139/40 | BDSC | 26007 | NO | ND |
| 121 | CG17167 | BDSC | 27245 | NO | ND |
| 122 | CG1718 | BDSC | 38329 | NO | ND |
| 123 | CG1724 | VDRC | 30315 | NO | ND |
| 124 | CG17300 | VDRC | 6521 | NO | ND |
| 125 | CG17637 | VDRC | 102424 | NO | ND |
| 127 | CG17662 | VDRC | 104067 | NO | ND |
| 128 | CG17664 | BDSC | 25924 | NO | ND |
| 129 | CG17751 | VDRC | 50914 | NO | ND |
| 130 | CG17752 | VDRC | 106787 | NO | ND |
| 131 | CG17922 | VDRC | 100882 | NO | ND |
| 132 | CG17929 | VDRC | 100093 | NO | ND |
| 133 | CG17930 | VDRC | 108912 | NO | ND |
| 134 | CG1801 | VDRC | 100868 | NO | ND |
| 135 | CG1824 | VDRC | 106935 | NO | ND |
| 136 | CG18281 | BDSC | 58222 | NO | ND |
| 137 | CG18317 | VDRC | 100807 | NO | ND |
| 138 | CG18324 | BDSC | 34720 | NO | ND |
| 139 | CG18327 | VDRC | 100920 | NO | ND |
| 140 | CG18347 | VDRC | 106319 | NO | ND |
| 141 | CG18418 | VDRC | 102109 | NO | ND |
| 142 | CG18788 | VDRC | 101610 | NO | ND |
| 143 | CG1907 | BDSC | 38998 | NO | ND |
| 144 | CG2003 | BDSC | 51699 | NO | ND |
| 145 | CG2177 | VDRC | 51083 | NO | ND |
| 146 | CG2187 | VDRC | 101065 | NO | ND |
| 147 | CG2316 | BDSC | 41984 | NO | ND |
| 148 | CG2616 | VDRC | 102630 | NO | ND |
| 149 | CG2663 | VDRC | 33548 | NO | ND |
| 150 | CG2893 | VDRC | 40987 | NO | ND |
| 152 | CG30194 | VDRC | 106140 | NO | ND |
| 153 | CG30265 | BDSC | 50731 | NO | ND |
| 154 | CG30272 | VDRC | 105475 | NO | ND |
| 155 | CG30339 | VDRC | 104772 | NO | ND |
| 156 | CG30344 | VDRC | 106870 | NO | ND |
| 157 | CG30345 | BDSC | 33994 | NO | ND |
| 158 | CG3036 | VDRC | 43179 | NO | ND |
| 159 | CG30392 | VDRC | 103584 | NO | ND |
| 160 | CG30394 | VDRC | 3470 | NO | ND |
| 161 | CG3091 | VDRC | 109832 | NO | ND |
| 162 | CG31100 | VDRC | 42627 | NO | ND |
| 163 | CG31103 | BDSC | 28359 | NO | ND |
| 164 | CG31106 | BDSC | 29582 | NO | ND |
| 165 | CG31121 | VDRC | 100046 | NO | ND |
| 167 | CG31262 | BDSC | 53970 | NO | ND |
| 168 | CG31272 | BDSC | 28030 | NO | ND |
| 169 | CG31321 | VDRC | 101856 | NO | ND |
| 171 | CG31547 | VDRC | 8552 | NO | ND |
| 172 | CG3156 | BDSC | 57727 | NO | ND |
| 173 | CG31636 | VDRC | 105018 | NO | ND |
| 175 | CG31668 | VDRC | 104093 | NO | ND |
| 177 | CG31693 | VDRC | 105558 | NO | ND |
| 178 | CG31731 | VDRC | 107135 | NO | ND |
| 179 | CG31787 | VDRC | 6372 | NO | ND |
| 180 | CG31792 | BDSC | 34942 | NO | ND |

TABLE 2-continued

| # | Symbol | Stock Center | RNAi Stock ID # | glue-GFP expression defect* | fat body cell migration defect** |
|---|---|---|---|---|---|
| 181 | CG31793 | BDSC | 38319 | NO | ND |
| 182 | CG31826 | VDRC | 100639 | NO | ND |
| 183 | CG31860 | VDRC | 103398 | NO | ND |
| 184 | CG31904 | BDSC | 34677 | NO | ND |
| 185 | CG3191 | VDRC | 109512 | NO | ND |
| 186 | CG32053 | VDRC | 107225 | NO | ND |
| 188 | CG32079 | VDRC | 104454 | NO | ND |
| 189 | CG32081 | VDRC | 107023 | NO | ND |
| 191 | CG32103 | VDRC | 108078 | NO | ND |
| 192 | CG32164/65 | BDSC | 60487 | NO | ND |
| 193 | CG32250 | VDRC | 108323 | NO | ND |
| 194 | CG32669 | VDRC | 102859 | NO | ND |
| 195 | CG3285 | VDRC | 51060 | NO | ND |
| 196 | CG33124 | VDRC | 105570 | NO | ND |
| 197 | CG33181 | BDSC | 38334 | NO | ND |
| 198 | CG33233 | VDRC | 106897 | NO | ND |
| 199 | CG33234 | VDRC | 106792 | NO | ND |
| 200 | CG33281 | VDRC | 7273 | NO | ND |
| 201 | CG33282 | VDRC | 100325 | NO | ND |
| 202 | CG33514 | VDRC | 47462 | NO | ND |
| 203 | CG33934/Indy-2 | BDSC | 34891 | NO | ND |
| 204 | CG3394 | BDSC | 56032 | NO | ND |
| 205 | CG33965 | VDRC | 61198 | NO | ND |
| 206 | CG33966 | VDRC | 104101 | NO | ND |
| 207 | CG33970 | BDSC | 60135 | NO | ND |
| 208 | CG3409 | VDRC | 37139 | NO | ND |
| 210 | CG34396 | BDSC | 26011 | NO | ND |
| 211 | CG3476 | BDSC | 60107 | NO | ND |
| 212 | CG3649 | BDSC | 44549 | NO | ND |
| 213 | CG3690 | BDSC | 27688 | NO | ND |
| 214 | CG3790 | VDRC | 108223 | NO | ND |
| 215 | CG3823 | VDRC | 107872 | NO | ND |
| 216 | CG3876 | VDRC | 44201 | NO | ND |
| 217 | CG4019 | VDRC | 107980 | NO | ND |
| 218 | CG42235 | BDSC | 50724 | NO | ND |
| 220 | CG42269 | VDRC | 101600 | NO | ND |
| 221 | CG42340 | BDSC | 27257 | NO | ND |
| 222 | CG42514 | VDRC | 45643 | NO | ND |
| 223 | CG42575 | VDRC | 107624 | NO | ND |
| 224 | CG42594 | BDSC | 35006 | NO | ND |
| 225 | CG42816 | VDRC | 106262 | NO | ND |
| 226 | CG42825 | VDRC | 5203 | NO | ND |
| 227 | CG4288 | VDRC | 104145 | NO | ND |
| 228 | CG43066 | BDSC | 28069 | NO | ND |
| 229 | CG43155 | BDSC | 55299 | NO | ND |
| 230 | CG4324 | VDRC | 109433 | NO | ND |
| 231 | CG4334 | VDRC | 106785 | NO | ND |
| 232 | CG43672 | VDRC | 48781 | NO | ND |
| 233 | CG44098 | VDRC | 100059 | NO | ND |
| 234 | CG4459 | VDRC | 107022 | NO | ND |
| 235 | CG4462 | VDRC | 105566 | NO | ND |
| 236 | CG4465 | VDRC | 100202 | NO | ND |
| 237 | CG4476 | BDSC | 38930 | NO | ND |
| 238 | CG4520 | VDRC | 34862 | NO | ND |
| 239 | CG4562 | VDRC | 32842 | NO | ND |
| 240 | CG4607 | VDRC | 107219 | NO | ND |
| 241 | CG4630 | VDRC | 101254 | NO | ND |
| 244 | CG4822 | BDSC | 25894 | NO | ND |
| 245 | CG4830 | BDSC | 57155 | NO | ND |
| 246 | CG4991 | BDSC | 44450 | NO | ND |
| 247 | CG4995 | VDRC | 106173 | NO | ND |
| 248 | CG5002 | BDSC | 55359 | NO | ND |
| 249 | CG5078 | BDSC | 57852 | NO | ND |
| 250 | CG5130 | VDRC | 5390 | NO | ND |
| 251 | CG5142 | VDRC | 22017 | NO | ND |
| 252 | CG5254 | BDSC | 50623 | NO | ND |
| 253 | CG5348 | VDRC | 101003 | NO | ND |
| 254 | CG5398 | VDRC | 109717 | NO | ND |
| 255 | CG5404 | VDRC | 100953 | NO | ND |
| 256 | CG5498 | VDRC | 103711 | NO | ND |
| 257 | CG5535 | VDRC | 107030 | NO | ND |
| 259 | CG5592 | VDRC | 110489 | NO | ND |
| 260 | CG5646 | BDSC | 33360 | NO | ND |
| 261 | CG5687 | VDRC | 33262 | NO | ND |
| 262 | CG5789 | BDSC | 57570 | NO | ND |
| 263 | CG5802 | VDRC | 103753 | NO | ND |
| 264 | CG5805 | BDSC | 57571 | NO | ND |
| 265 | CG5850 | VDRC | 1456 | NO | ND |
| 266 | CG5853 | BDSC | 27668 | NO | ND |
| 267 | CG5958 | VDRC | 100038 | NO | ND |
| 268 | CG5973 | VDRC | 24998 | NO | ND |
| 270 | CG6052 | VDRC | 106738 | NO | ND |
| 271 | CG6125 | VDRC | 107894 | NO | ND |
| 272 | CG6126 | BDSC | 56038 | NO | ND |
| 273 | CG6231 | VDRC | 105194 | NO | ND |
| 274 | CG6293 | VDRC | 108619 | NO | ND |
| 275 | CG6299 | VDRC | 109737 | NO | ND |
| 276 | CG6300 | BDSC | 55264 | NO | ND |
| 279 | CG6484 | BDSC | 60372 | NO | ND |
| 280 | CG6499 | VDRC | 100416 | NO | ND |
| 281 | CG6565 | VDRC | 39006 | NO | ND |
| 282 | CG6672 | VDRC | 107388 | NO | ND |
| 283 | CG6723 | BDSC | 29425 | NO | ND |
| 284 | CG6812 | VDRC | 103925 | NO | ND |
| 285 | CG6836 | VDRC | 108502 | NO | ND |
| 286 | CG6893 | VDRC | 102093 | NO | ND |
| 287 | CG6901 | VDRC | 104673 | NO | ND |
| 288 | CG6928 | BDSC | 50552 | NO | ND |
| 289 | CG6978 | VDRC | 7041 | NO | ND |
| 290 | CG7084 | BDSC | 42767 | NO | ND |
| 291 | CG7091 | VDRC | 102183 | NO | ND |
| 292 | CG7255 | BDSC | 58352 | NO | ND |
| 293 | CG7272 | VDRC | 41950 | NO | ND |
| 295 | CG7333 | BDSC | 57433 | NO | ND |
| 296 | CG7342 | VDRC | 48001 | NO | ND |
| 297 | CG7442 | BDSC | 35817 | NO | ND |
| 298 | CG7448 | VDRC | 102236 | NO | ND |
| 299 | CG7458 | BDSC | 35237 | NO | ND |
| 300 | CG7514 | VDRC | 103023 | NO | ND |
| 301 | CG7627 | BDSC | 32337 | NO | ND |
| 302 | CG7708 | VDRC | 28613 | NO | ND |
| 303 | CG7777 | BDSC | 50695 | NO | ND |
| 304 | CG7806 | BDSC | 38997 | NO | ND |
| 305 | CG7816 | VDRC | 1364 | NO | ND |
| 306 | CG7881 | BDSC | 44505 | NO | ND |
| 307 | CG7882 | VDRC | 109918 | NO | ND |
| 308 | CG7888 | VDRC | 37263 | NO | ND |
| 309 | CG7912 | VDRC | 1378 | NO | ND |
| 310 | CG7943 | VDRC | 28632 | NO | ND |
| 311 | CG8008 | VDRC | 4159 | NO | ND |
| 312 | CG8026 | VDRC | 105681 | NO | ND |
| 313 | CG8028 | VDRC | 102317 | NO | ND |
| 314 | CG8034 | BDSC | 32340 | NO | ND |
| 315 | CG8046 | VDRC | 7380 | NO | ND |
| 316 | CG8219 | VDRC | 103487 | NO | ND |
| 317 | CG8249 | VDRC | 106077 | NO | ND |
| 318 | CG8323 | VDRC | 4861 | NO | ND |
| 319 | CG8389 | VDRC | 107639 | NO | ND |
| 320 | CG8451 | VDRC | 104177 | NO | ND |
| 321 | CG8468 | VDRC | 6452 | NO | ND |
| 322 | CG8596 | BDSC | 55664 | NO | ND |
| 323 | CG8602 | VDRC | 101575 | NO | ND |
| 324 | CG8632 | VDRC | 108929 | NO | ND |
| 325 | CG8654 | BDSC | 57428 | NO | ND |
| 327 | CG8785 | VDRC | 4651 | NO | ND |
| 328 | CG8791 | VDRC | 7945 | NO | ND |
| 329 | CG8837 | VDRC | 100670 | NO | ND |
| 330 | CG8850 | VDRC | 104098 | NO | ND |
| 331 | CG8860 | BDSC | 60127 | NO | ND |
| 332 | CG8908 | BDSC | 41850 | NO | ND |
| 333 | CG8925 | VDRC | 101128 | NO | ND |
| 334 | CG9090 | BDSC | 44495 | NO | ND |
| 335 | CG9194 | BDSC | 25921 | NO | ND |
| 336 | CG9254 | VDRC | 13409 | NO | ND |
| 337 | CG9270 | BDSC | 34029 | NO | ND |
| 338 | CG9281 | BDSC | 58189 | NO | ND |
| 339 | CG9308 | VDRC | 6606 | NO | ND |
| 340 | CG9317 | BDSC | 57730 | NO | ND |
| 341 | CG9330 | BDSC | 57795 | NO | ND |
| 342 | CG9396 | VDRC | 104068 | NO | ND |
| 343 | CG9399 | VDRC | 101455 | NO | ND |
| 344 | CG9413 | BDSC | 51791 | NO | ND |

TABLE 2-continued

| # | Symbol | Stock Center | RNAi Stock ID # | glue-GFP expression defect* | fat body cell migration defect** |
|---|---|---|---|---|---|
| 345 | CG9430 | VDRC | 110047 | NO | ND |
| 346 | CG9444 | VDRC | 104529 | NO | ND |
| 347 | CG9582 | VDRC | 100256 | NO | ND |
| 348 | CG9657 | BDSC | 28384 | NO | ND |
| 349 | CG9663 | VDRC | 62192 | NO | ND |
| 350 | CG9664 | VDRC | 42467 | NO | ND |
| 351 | CG9702 | VDRC | 6860 | NO | ND |
| 352 | CG9706 | BDSC | 51908 | NO | ND |
| 354 | CG9825 | BDSC | 50639 | NO | ND |
| 355 | CG9826 | BDSC | 51728 | NO | ND |
| 356 | CG9864 | VDRC | 103970 | NO | ND |
| 357 | CG9903 | VDRC | 42689 | NO | ND |
| 358 | CG9990 | VDRC | 107544 | NO | ND |
| 359 | CHOp24 | VDRC | 100274 | NO | ND |
| 360 | cm | BDSC | 27282 | NO | ND |
| 362 | colt | BDSC | 51798 | NO | ND |
| 365 | Cralbp | VDRC | 31258 | NO | ND |
| 366 | Csat | BDSC | 44488 | NO | ND |
| 368 | Ctr1B | BDSC | 57710 | NO | ND |
| 369 | Ctr1C | VDRC | 102136 | NO | ND |
| 370 | cv-d | VDRC | 3975 | NO | ND |
| 371 | DAT | BDSC | 50619 | NO | ND |
| 372 | Dic1 | VDRC | 103757 | NO | ND |
| 373 | Dic2 | VDRC | 104152 | NO | ND |
| 374 | Dic3 | VDRC | 100255 | NO | ND |
| 375 | Dic4 | VDRC | 8416 | NO | ND |
| 376 | dmGlut | BDSC | 36724 | NO | ND |
| 377 | Drip | BDSC | 44661 | NO | ND |
| 378 | E23 | BDSC | 57782 | NO | ND |
| 379 | Eaat1 | BDSC | 43287 | NO | ND |
| 380 | Eaat2 | BDSC | 40832 | NO | ND |
| 381 | eag | BDSC | 31678 | NO | ND |
| 382 | eca | VDRC | 101388 | NO | ND |
| 383 | Efr | VDRC | 30238 | NO | ND |
| 384 | Elk | BDSC | 25821 | NO | ND |
| 386 | Ent1 | BDSC | 51055 | NO | ND |
| 387 | Ent2 | VDRC | 100464 | NO | ND |
| 388 | Ent3 | VDRC | 47537 | NO | ND |
| 389 | Esp | VDRC | 9795 | NO | ND |
| 394 | Fbp1 | VDRC | 37881 | NO | ND |
| 396 | frc | BDSC | 42007 | NO | ND |
| 397 | Fs(2)Ket | BDSC | 41845 | NO | ND |
| 399 | G31689 | BDSC | 57778 | NO | ND |
| 400 | galectin | BDSC | 34880 | NO | ND |
| 401 | gb | VDRC | 1262 | NO | ND |
| 402 | Gfr | VDRC | 105410 | NO | ND |
| 403 | Gga | BDSC | 51170 | NO | ND |
| 404 | globl | BDSC | 36668 | NO | ND |
| 405 | Glut1 | BDSC | 40904 | NO | ND |
| 406 | Glut3 | VDRC | 100253 | NO | ND |
| 407 | Hmt-1 | BDSC | 53284 | NO | ND |
| 408 | hoe1 | BDSC | 33377 | NO | ND |
| 409 | hoe2 | BDSC | 28661 | NO | ND |
| 410 | Ih | BDSC | 58089 | NO | ND |
| 411 | Indy | VDRC | 9981 | NO | ND |
| 413 | Jwa | VDRC | 6375 | NO | ND |
| 414 | kar | VDRC | 105429 | NO | ND |
| 416 | l(2)03659 | VDRC | 100105 | NO | ND |
| 417 | l(2)08717 | VDRC | 11117 | NO | ND |
| 418 | List | VDRC | 109791 | NO | ND |
| 419 | loj | BDSC | 57702 | NO | ND |
| 420 | Mct1 | VDRC | 106773 | NO | ND |
| 422 | Mdr50 | BDSC | 35034 | NO | ND |
| 423 | Mdr65 | BDSC | 35035 | NO | ND |
| 424 | mfrn | BDSC | 34038 | NO | ND |
| 425 | MFS10 | BDSC | 34562 | NO | ND |
| 426 | MFS15 | VDRC | 106207 | NO | ND |
| 427 | MFS16 | VDRC | 108635 | NO | ND |
| 428 | MFS17 | VDRC | 44033 | NO | ND |
| 429 | MFS18 | BDSC | 33998 | NO | ND |
| 430 | MFS3 | VDRC | 107656 | NO | ND |
| 433 | Mpcp | BDSC | 44508 | NO | ND |
| 434 | MRP | BDSC | 38316 | NO | ND |
| 435 | Mrp4 | BDSC | 60136 | NO | ND |
| 436 | MSBP | VDRC | 45185 | NO | ND |
| 438 | Mtch | BDSC | 38986 | NO | ND |
| 439 | Mtp | BDSC | 51872 | NO | ND |
| 440 | Mvl | BDSC | 55316 | NO | ND |
| 441 | na | BDSC | 25808 | NO | ND |
| 442 | NAAT1 | VDRC | 50064 | NO | ND |
| 443 | NaPi-T | BDSC | 34003 | NO | ND |
| 444 | Ncc69 | BDSC | 28682 | NO | ND |
| 445 | Nckx30C | BDSC | 42581 | NO | ND |
| 446 | Ndae1 | VDRC | 102707 | NO | ND |
| 447 | Nha1 | BDSC | 42648 | NO | ND |
| 448 | Nhe1 | BDSC | 28589 | NO | ND |
| 449 | Nhe2 | BDSC | 51491 | NO | ND |
| 450 | Nhe3 | BDSC | 50513 | NO | ND |
| 451 | Ntl | VDRC | 102776 | NO | ND |
| 452 | Oatp26F | VDRC | 2650 | NO | ND |
| 453 | Oatp30B | VDRC | 22983 | NO | ND |
| 454 | Oatp33Ea | BDSC | 50736 | NO | ND |
| 455 | Oatp33Eb | VDRC | 100431 | NO | ND |
| 456 | Oatp58Da | BDSC | 44122 | NO | ND |
| 457 | Oatp58Db | VDRC | 100348 | NO | ND |
| 458 | Oatp58Dc | BDSC | 44583 | NO | ND |
| 460 | opm | BDSC | 43280 | NO | ND |
| 461 | or | BDSC | 55218 | NO | ND |
| 463 | Orct2 | BDSC | 57583 | NO | ND |
| 464 | out | VDRC | 108364 | NO | ND |
| 465 | p115 | VDRC | 44510 | NO | ND |
| 466 | p24-1 | BDSC | 57776 | NO | ND |
| 467 | p24-2 | VDRC | 109179 | NO | ND |
| 468 | para | BDSC | 33923 | NO | ND |
| 469 | path | VDRC | 100519 | NO | ND |
| 471 | PGRP-LC | BDSC | 33383 | NO | ND |
| 472 | Picot | BDSC | 25920 | NO | ND |
| 473 | PMCA | BDSC | 31572 | NO | ND |
| 474 | Pmp70 | BDSC | 34349 | NO | ND |
| 475 | Prestin | BDSC | 50706 | NO | ND |
| 476 | prt | VDRC | 104763 | NO | ND |
| 477 | rb | BDSC | 32477 | NO | ND |
| 478 | rdgB | BDSC | 28796 | NO | ND |
| 479 | rdgBbeta | BDSC | 44523 | NO | ND |
| 480 | retm | VDRC | 44687 | NO | ND |
| 481 | Rfabg | BDSC | 28946 | NO | ND |
| 482 | Rh50 | BDSC | 50666 | NO | ND |
| 484 | rtet | VDRC | 110473 | NO | ND |
| 485 | salt | VDRC | 108782 | NO | ND |
| 486 | ScpX | BDSC | 51479 | NO | ND |
| 487 | Sec24AB | VDRC | 107154 | NO | ND |
| 489 | SerT | VDRC | 100584 | NO | ND |
| 490 | sesB | BDSC | 36661 | NO | ND |
| 491 | Shawn | VDRC | 109948 | NO | ND |
| 492 | Slc45-1 | VDRC | 105439 | NO | ND |
| 493 | slif | VDRC | 45590 | NO | ND |
| 494 | sll | VDRC | 12148 | NO | ND |
| 495 | Sln | VDRC | 109464 | NO | ND |
| 496 | slo | BDSC | 55405 | NO | ND |
| 497 | sly | BDSC | 29388 | NO | ND |
| 498 | Smvt | VDRC | 102662 | NO | ND |
| 499 | spict | BDSC | 37505 | NO | ND |
| 500 | spin | BDSC | 27702 | NO | ND |
| 501 | st | BDSC | 60134 | NO | ND |
| 502 | Start1 | VDRC | 4053 | NO | ND |
| 503 | sug | BDSC | 55182 | NO | ND |
| 504 | Sur | BDSC | 36087 | NO | ND |
| 505 | Surf1 | BDSC | 51783 | NO | ND |
| 507 | sut1 | VDRC | 104983 | NO | ND |
| 508 | sut2 | BDSC | 28207 | NO | ND |
| 509 | sut3 | VDRC | 4009 | NO | ND |
| 510 | sut4 | VDRC | 44935 | NO | ND |
| 511 | TM9SF4 | BDSC | 54019 | NO | ND |
| 512 | Tpc1 | BDSC | 31749 | NO | ND |
| 513 | Tpc2 | VDRC | 107215 | NO | ND |
| 514 | Tret1-1 | BDSC | 42880 | NO | ND |
| 515 | Tret1-2 | VDRC | 49889 | NO | ND |
| 516 | Trn | BDSC | 50732 | NO | ND |
| 517 | Tm-SR | BDSC | 56974 | NO | ND |
| 518 | Tyler | VDRC | 50573 | NO | ND |
| 519 | Ucp4A | VDRC | 102571 | NO | ND |
| 521 | Ucp4C | VDRC | 100064 | NO | ND |

TABLE 2-continued

| # | Symbol | Stock Center | RNAi Stock ID # | glue-GFP expression defect* | fat body cell migration defect** |
|---|---|---|---|---|---|
| 522 | VAChT | BDSC | 27684 | NO | ND |
| 523 | VGlut | BDSC | 40845 | NO | ND |
| 524 | VhaAC39-2 | VDRC | 34303 | NO | ND |
| 525 | VhaM9.7-c | BDSC | 26004 | NO | ND |
| 526 | VhaM9.7-d | VDRC | 106115 | NO | ND |
| 529 | w | BDSC | 33623 | NO | ND |
| 530 | wun2 | BDSC | 32423 | NO | ND |
| 531 | yin | BDSC | 31971 | NO | ND |
| 532 | ZIP1 | VDRC | 107309 | NO | ND |
| 533 | Zip3 | VDRC | 37358 | NO | ND |
| 534 | ZnT35C | BDSC | 39049 | NO | ND |
| 535 | ZnT63C | VDRC | 105145 | NO | ND |
| 536 | β'COP | BDSC | 36113 | NO | ND |
| 187 | CG32054 | VDRC | 107214 | Lethal | ND |
| 353 | CG9717 | VDRC | 42669 | Lethal | ND |
| 412 | JhI-21 | BDSC | 41706 | Lethal | ND |
| 415 | kcc | BDSC | 34584 | Lethal | ND |
| 488 | Sec24CD | VDRC | 106929 | Lethal | ND |
| 537 | ζCOP | BDSC | 28960 | Lethal | ND |

*(in any animal observed)
**(in all animals observed, with no other obvious defects)
ND = not determined Example 2

Study of EcI in *D. melanogaster* Cells

Using RNAi, the role of EcI in the transport of 20-hydroxyecdysone (20E) was investigated in *D. melanogaster*.

The steroid 20E is the primary steroid hormone in insects, which triggers molting and metamorphosis in the larval stage.

Figure 1B:
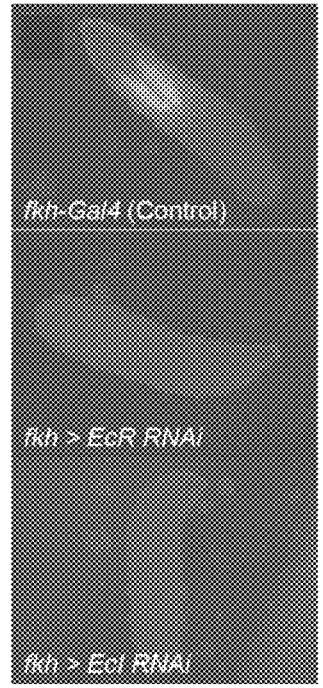
FIG. 1B is an image of in vivo RNAi screening in wandering stage larvae of D. melanogaster, showing green-fluorescent protein (GFP) signal in the salivary gland in the presence and absence of ecdysone importer (EcI) and ecdysone reporter (EcR) RNAi. The GFP signal is from glue-GFP, the expression of which in the salivary gland is typically induced by 20E during the wandering stage. fkh-Gal4 is a salivary gland-specific Gal4 driver.

RNAi of ecdysone receptor (EcR; encoding the nuclear receptor for 20E) or EcI using the SG-specific driver (fkh-Gal4) resulted in the loss of 20E-dependent glue-GFP expression in the SG in wandering stage larvae (FIG. 1B). SG cells remained intact in both cases.

Figure 1C:
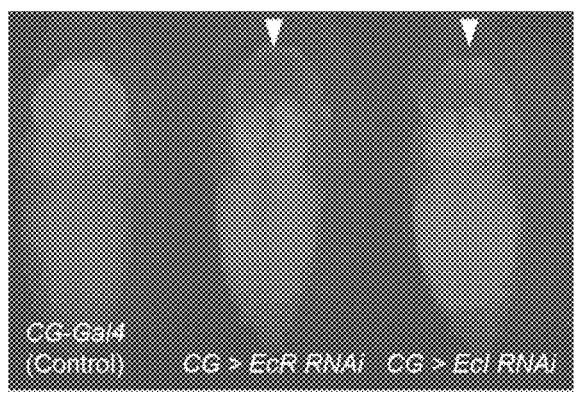
FIG. 1C is an image of in vivo RNAi screening in the white prepupal stage of D. melanogaster, showing the distribution of fat body (FB) cells that typically migrate into the pupal head in response to 20E. FB cells are labeled with GFP; lack of FB cell migration into the pupal head is indicated by the arrowheads.

RNAi of EcR or EcI in the FB prevented ecdysone-dependent FB cell migration into the pupal head (FIG. 1C).

Figure 1D:
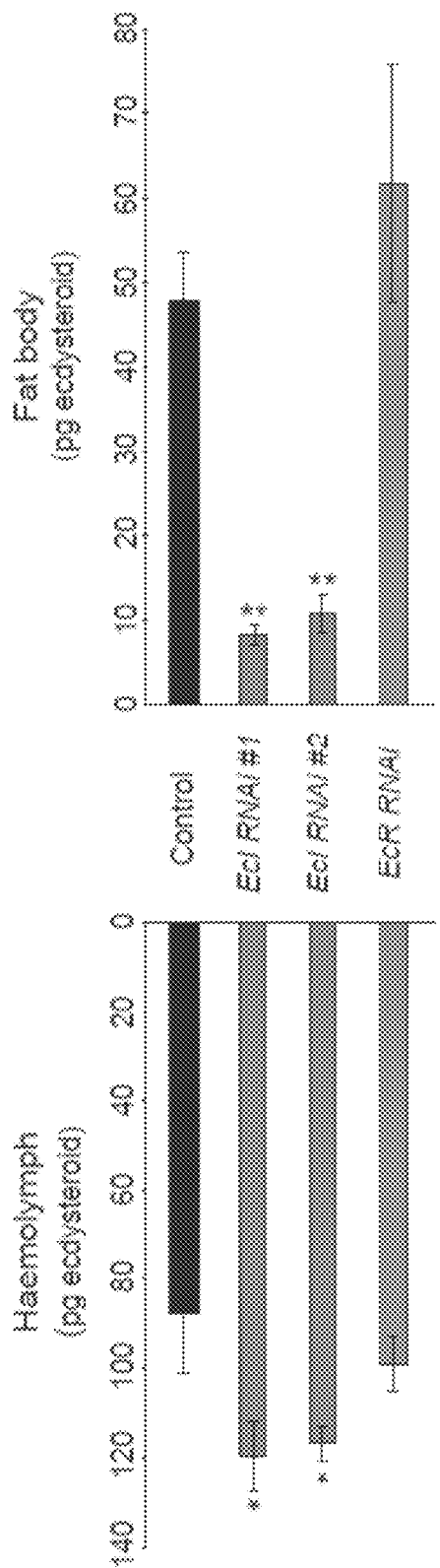
FIG. 1D is a graph showing the level of ecdysteroids in the FB or hemolymph of white prepupae with knockdown of EcI, knockdown of EcR, or no knockdown in the FB. Each bar represents mean±SEM; * indicates $p<0.05$ from Student's t-test compared to control; ** indicates $p<0.01$ from Student's t-test compared to control.

Knockdown of EcI, but not EcR, in the FB reduced the intracellular level of ecdysteroids (steroids including 20E) in the tissue, whereas it did not affect the hemolymph level of ecdysteroids in the white prepupal stage (FIG. 1D).

Thus, it was found that a gene knockdown of EcI in the salivary gland and fat body tissues of *D. melanogaster* caused similar effects to the knockdown of ecdysone receptor (EcR), which encodes the nuclear receptor for 20E.

Figure 2A:
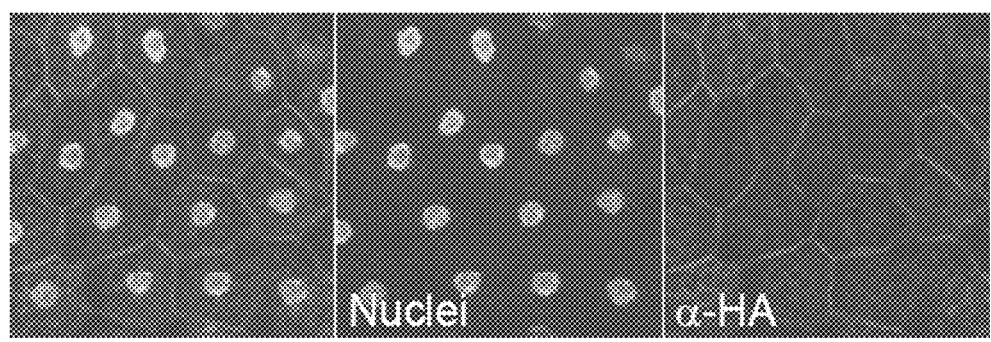
FIG. 2A is an image of overexpression of Flag-HA-tagged EcI (CG-Gal4>UAS-Oatp74D-Flag-HA) in D. melanogaster FB cells. The middle panel depicts the signal from the cell nuclei (stained using Hoechst 33342), while the right panel depicts the signal from $\alpha$-HA.
Figure 2B:
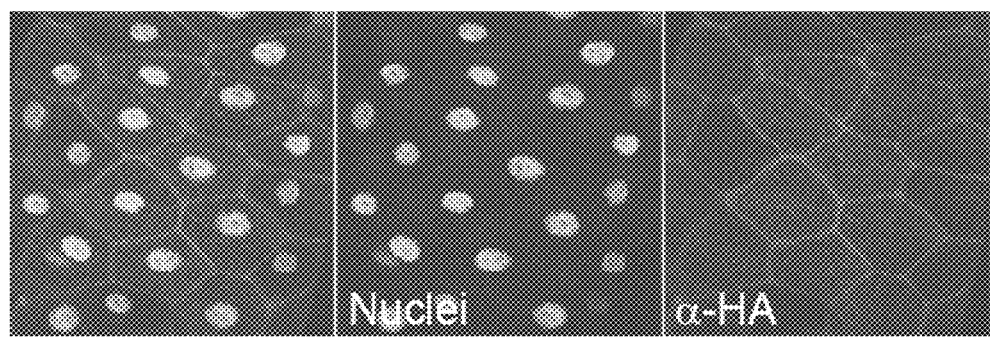
FIG. 2B is an image of overexpression of Flag-HA-tagged EcI (fkh-Gal4>UAS-Oatp74D-Flag-HA) in D. melanogaster salivary gland cells. The middle panel depicts the signal from the cell nuclei (stained using Hoechst 33342), while the right panel depicts the signal from $\alpha$-HA.

Next, Flag-HA-tagged EcI was overexpressed in FB cells (CG-Gal4>UAS-Oatp74D-Flag-HA). FIG. 2A is an image of the FB cells, in which the flag-HA tagged EcI can be seen localized at the cellular membrane. Flag-HA-tagged EcI was also overexpressed in SG cells (fkh-Gal4>UAS-Oatp74D-Flag-HA). As shown in FIG. 2B, the tagged EcI was also localized at the cellular membrane in the SG cells. These findings support the conclusion that EcI encodes a 20E importer. The incorporated amount of ecdysteroids (steroids including 20E) in the fat body was reduced when the expression of EcI was suppressed (FIG. 1D).

Example 3

Study of EcI in Culture Cell Lines

The expression of EcI was next evaluated in the *Drosophila* S2 culture cells and human HEK culture cells.

Figure 3:
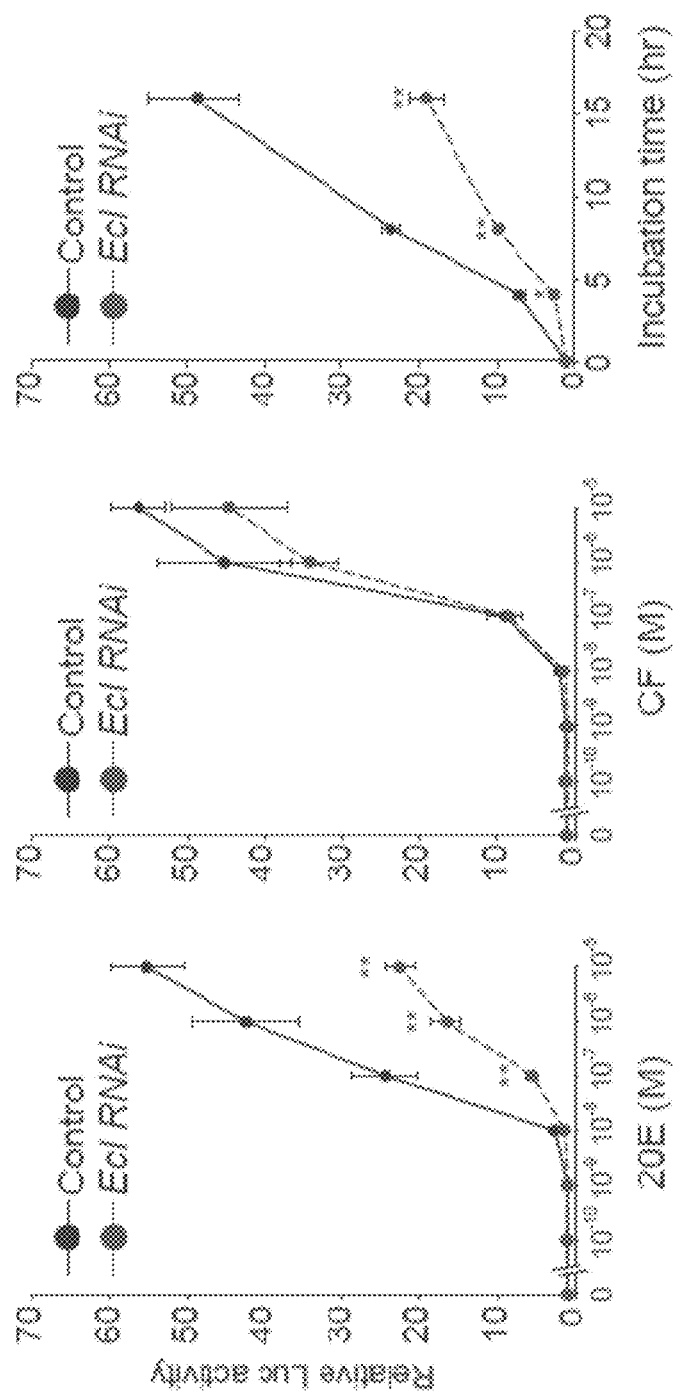
FIG. 3 is a graph of the fold change of D. melanogaster EcR response after incubation of S2 culture cells for 24 hours in varying concentrations of 20E (left graph) or chromafenozide (CF; middle graph), as measured by luciferase reporter assay. The right graph is a time-course analysis of EcR-mediated luciferase activity in S2 culture cells treated with $10^{-7}$M of 20E. In each graph, the control data is the solid top line, and the dashed bottom line is data of cells treated with EcI RNAi. Each point represents mean±SD; * indicates $p<0.05$ from Student's t-test compared to control; ** indicates $p<0.01$ from Student's t-test compared to control.

S2 culture cells treated with EcI RNAi were incubated with varying concentrations of 20E or with chromafenozide (CF) for 24 hours, and their response was monitored using a luciferase reporter assay. The relative response of the treated cells was compared to control cells, which were incubated with 20E or CF but not treated with RNAi. As shown in the left and middle graphs of FIG. 3, RNAi treatment significantly decreased the cells' response to 20E as measured by the luciferase assay, but had less effect on response to CF. CF is a non-steroidal EcR agonist, and is expected to enter the cells through an unknown transporter distinct from EcI. A time-course analysis of luciferase activity in S2 cells treated with $10^{-7}$ M 20E and with or without RNAi was also performed (FIG. 3, right graph), which showed RNAi treatment significantly decreased the cells' response to 20E over time.

Figure 4:
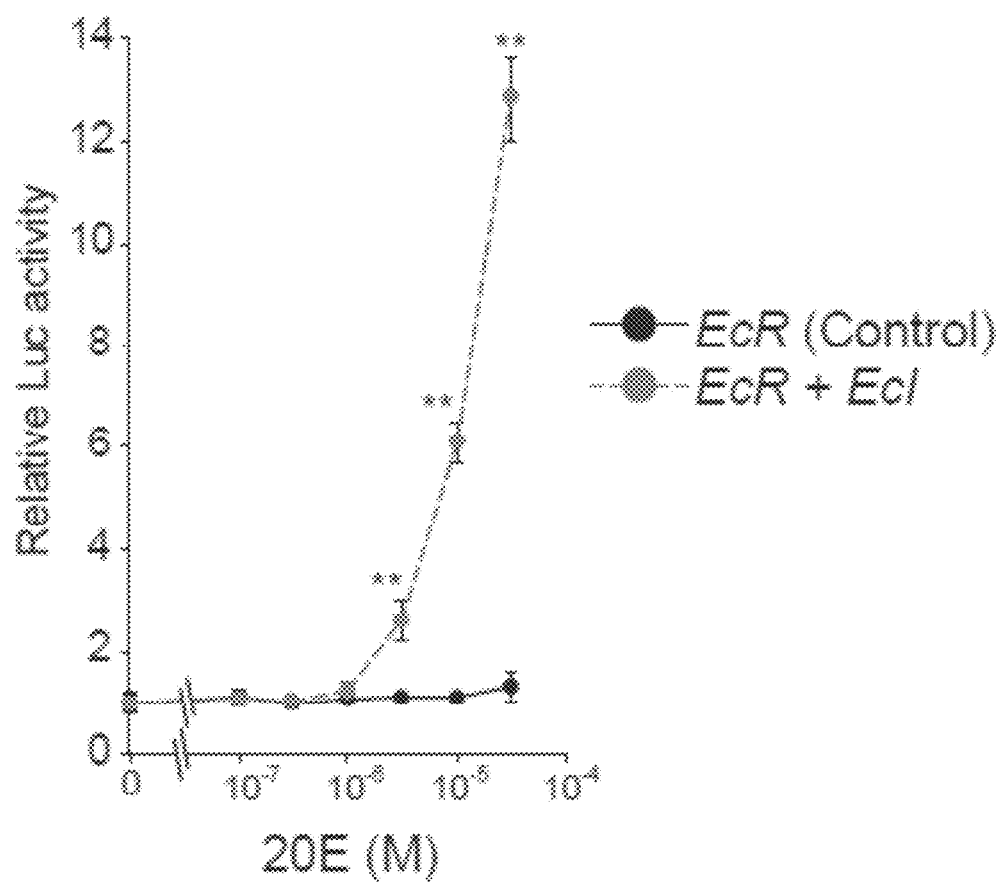
FIG. 4 is a relative luciferase reporter activity in HEK culture cells treated for 24 h with 20E. Response of the cells transfected with EcR is the solid bottom line; cells transfected with EcR and EcI is the dashed top line. Each point represents mean±SEM; ** indicates $p<0.01$ from Student's t-test compared to control.

Human HEK cells were transfected with EcI and EcR, and their response to incubation with varying concentrations of 20E for 24 hours was evaluated using the luciferase reporter assay. Control HEK cells that were transfected only with EcR were also evaluated. As shown in FIG. 4, the control HEK cells are not responsive to 20E as measured by luciferase assay (solid bottom line), while HEK cells transfected with both EcI and EcR were responsive (dashed top line). These results demonstrate that EcI incorporates 20E into animal cells.

What is claimed is:

1. A method of identifying a compound that can modulate the transport of a steroid hormone across a phospholipid membrane, comprising:
    providing a steroid hormone to an initial cell and a comparative cell in either the presence or absence of a candidate compound, wherein the initial cell expresses a steroid hormone transporter gene, and the expression of the steroid hormone transporter gene in the comparative cell is absent or lower than in the initial cell;
    determining the amount of the steroid hormone that is transported across the phospholipid membrane of the initial cell and the comparative cell;
    observing a difference between the amount of steroid hormone that is transported across the phospholipid membrane of the initial cell in the presence of the candidate compound compared to the absence of the candidate compound;
    comparing the difference to the amount of steroid hormone that is transported across the phospholipid membrane of the comparative cell in the presence or absence of the candidate compound, and
    determining that the candidate compound can modulate the transport of a steroid hormone across a phospholipid membrane if the amount of steroid hormone that is transported across the phospholipid membrane is different in the initial cell than in the comparative cell,
    wherein the steroid hormone transporter gene is ecdysone importer (EcI).

2. The method of claim 1, wherein the difference in the amount of steroid hormone transported across the phospholipid membrane is determined using a luciferase reporter assay.

3. The method of claim 1, wherein the expression of the steroid hormone transporter gene in the comparative cell is absent, and the method further comprises transfecting the initial cell, the comparative cell, or both with cDNA comprising the steroid hormone transporter gene.

4. The method of claim 1, further comprising transfecting the initial cell, the comparative cell, or both with cDNA comprising a steroid hormone nuclear receptor gene.

5. The method of claim 4, wherein the steroid hormone nuclear receptor gene is ecdysone receptor (EcR).

6. The method of claim 1, wherein the initial cell and the comparative cell are from an arthropod cell line or a mammalian cell line.

7. The method of claim 1, wherein the steroid hormone is an ecdysteroid.

8. The method of claim 1, wherein the steroid hormone is 20-hydroxyecdysone.

9. The method of claim 1, wherein the expression of the steroid hormone transporter gene in the comparative cell is lower than in the initial cell.

10. The method of claim 9, wherein the expression of the steroid hormone transporter gene in the comparative cell is reduced using RNAi.

11. A method of identifying a compound that can affect the transcriptional activity of a steroid hormone nuclear receptor, comprising:
providing a steroid hormone to an initial cell and a comparative cell in either the presence or absence of a candidate compound, wherein the initial cell expresses a steroid hormone transporter gene, and the expression of the steroid hormone transporter gene in the comparative cell is absent or lower than in the initial cell;
determining the transcriptional activity of the steroid hormone nuclear receptor in the initial cell and the comparative cell;
observing a difference between the transcriptional activity in the initial cell in the presence of the candidate compound compared to the absence of the candidate compound;
comparing the difference to the transcriptional activity of the comparative cell in the presence or absence of the candidate compound, and
determining that the candidate compound can affect the transcriptional activity of a steroid hormone nuclear receptor if the amount of transcriptional activity is different in the initial cell than in the comparative cell, wherein the steroid hormone transporter gene is ecdysone importer (EcI).

12. The method of claim 11, wherein the difference in the transcriptional activity is determined using a luciferase reporter assay.

13. The method of claim 11, wherein the expression of the steroid hormone transporter gene in the comparative cell is absent, and the method further comprises transfecting the initial cell, the comparative cell, or both with cDNA comprising the steroid hormone transporter gene.

14. The method of claim 11, further comprising transfecting the initial cell, the comparative cell, or both with cDNA comprising the steroid hormone nuclear receptor gene.

15. The method of claim 11, wherein the steroid hormone nuclear receptor gene is ecdysone receptor (EcR).

16. The method of claim 11, wherein the initial cell and the comparative cell are from an arthropod cell line or a mammalian cell line.

17. The method of claim 11, wherein the steroid hormone is an ecdysteroid.

18. The method of claim 11, wherein the steroid hormone is 20-hydroxyecdysone.

19. The method of claim 11, wherein the expression of the steroid hormone transporter gene in the comparative cell is lower than in the initial cell.

20. The method of claim 19, wherein the expression of the steroid hormone transporter gene in the comparative cell is reduced using RNAi.

* * * * *